(12) United States Patent
Block et al.

(10) Patent No.: US 6,307,125 B1
(45) Date of Patent: Oct. 23, 2001

(54) NUCLEIC ACID MOLECULES ENCODING ENZYMES FROM WHEAT WHICH ARE INVOLVED IN STARCH SYNTHESIS

(75) Inventors: Martina Block, Bonn; Horst Lörz; Stephanie Lütticke, both of Hamburg; Lennart Walter, Glückstadt; Claus Frohberg, Berlin; Jens Kossmann, Golm, all of (DE)

(73) Assignee: Hoechst Schering AgrEvo, GmbH, Berlin (DE)

( * ) Notice: Subject to any disclaimer, the term of this patent is extended or adjusted under 35 U.S.C. 154(b) by 0 days.

(21) Appl. No.: 09/196,390

(22) Filed: Nov. 19, 1998

Related U.S. Application Data

(63) Continuation of application No. PCT/EP97/02793, filed on May 28, 1997.

(30) Foreign Application Priority Data

May 29, 1996 (DE) .............................................. 196 21 588
Sep. 11, 1996 (DE) .............................................. 196 36 917

(51) Int. Cl.[7] .............................. C12N 15/29; C12N 5/04; C12N 15/82; A01H 5/00; C12P 19/04
(52) U.S. Cl. ....................... 800/284; 800/278; 800/317.2; 800/320; 800/320.1; 800/320.2; 800/320.3; 435/69.1; 435/320.1; 435/419; 536/23.6
(58) Field of Search .......................... 536/23.6; 435/69.1, 435/320.1, 419; 800/284, 320.3, 278, 317.2, 320, 320.1, 320.2

(56) References Cited

U.S. PATENT DOCUMENTS 5,349,123 * 9/1994 Shewmaker et al. ................ 800/205
5,824,790 * 10/1998 Keeling et al. ..................... 536/23.6

FOREIGN PATENT DOCUMENTS 44 41 408 A1  5/1996 (DE) .............................. C12N/15/82
0 521 621 A2  1/1993 (EP) .............................. C12N/15/11

OTHER PUBLICATIONS

Clark et al. Plant Mol. Biol. 16(6):1099–1101, 1991.*
Dry et al. Plant J. 2(2):193–202, 1992.*
Baba et al. Plant Physiol. 103:565–573, 1993.*
Nakatani et al. Jpn. J. Crop Sci. 61(3):463–468, 1992.*
Kossmann et al. Progress Biotechnol. 10:271–278, 1995.*
C. Ainsworth et al., "Expression, Organisation and Structure of the Genes Encoding the Waxy Protein (Granule–Bound Starch Synthase) in Wheat," *Plant Molecular Biology*, 22, pp. 67–82 (1993).
K. Denyer et al., "Identification of Multiple Isoforms of Soluble and Granule–Bound Starch Synthase in Developing Wheat Endosperm," *Planta*, 196, pp. 256–265 (1995).
S. Rahman, et al., "The Major Proteins of Wheat Endosperm Starch Granules," *Australian Journal of Plant Physiology*, 22, pp. 793–803 (1995).
J. Clark et al., "Wheat Waxy mRNA for Granule–Bound Starch Synthase," *EMBL Database*, AC X57233 (1991).

* cited by examiner

Primary Examiner—David T. Fox
(74) Attorney, Agent, or Firm—Fish & Neave; James F. Haley, Jr.; Elinor K. Shin

(57) ABSTRACT

The present invention relates to nucleic acid molecules encoding enzymes which are involved in the starch synthesis in plants. These enzymes are starch synthases from wheat. The invention further relates to vectors and host cells containing said nucleic acid molecules, in particular transformed plant cells and plants regenerated from these cells, which exhibit an increased or a reduced activity of the described starch synthases.

29 Claims, No Drawings

NUCLEIC ACID MOLECULES ENCODING ENZYMES FROM WHEAT WHICH ARE INVOLVED IN STARCH SYNTHESIS

This application is a continuation of international application PCT/EP97/02793, filed on May 28, 1997, which designated the United States.

FIELD OF THE INVENTION

The present invention relates to nucleic acid molecules encoding enzymes from wheat which are involved in the starch synthesis of plants. These enzymes are isotypes of the starch synthase.

The invention further relates to vectors and bacteria which contain these nucleic acid molecules as well as plant cells and plants transformed with the described nucleic acid molecules. Furthermore, methods for the production of transgenic plants are described which due to the integration of DNA molecules encoding starch synthase from wheat, synthesize starch which is modified in its properties.

With respect to its increasing significance which has recently been ascribed to vegetal substances as regenerative sources of raw materials, one of the objects of biotechnological research is to try to adapt vegetal raw materials to the demands of the processing industry. In order to enable the use of modified regenerative raw materials in as many areas as possible, it is furthermore important to obtain a large variety of substances. Apart from oils, fats and proteins, polysaccharides constitute the essential regenerative raw materials derived from plants. Apart from cellulose, starch maintains an important position among the polysaccharides, being one of the most significant storage substances in higher plants. Among those, wheat is an interesting cultivated plant as it generates 20% of the total amount of starch produced in the European Community.

The polysaccharide starch is a polymer made up of chemically homogeneous basic components, namely the glucose molecules. However, it constitutes a highly complex mixture from various types of molecules which differ from each other in their degree of polymerization and in the degree of branching of the glucose chains. Therefore, starch is not a homogeneous raw material. One differentiates particularly between amylose-starch, a basically non-branched polymer made up of α-1,4-glycosidically branched glucose molecules, and amylopectin-starch which in turn is a complex mixture of various branched glucose chains. The branching results from additional α-1,6-glycosidic interlinkings. In wheat the synthesized starch consists of about 11–37% of amylose-starch, depending on the cultivar. In order to enable as wide a use of starch as possible, it seems to be desirable that plants be provided which are capable of synthesizing modified starch which is particularly suitable for various uses. Breeding is one possibility to provide such plants. This, however, turns out to be very difficult in the case of wheat due to the polyploid properties of cultivated wheat (tetra- and hexaploid). Only recently scientists succeeded in producing "waxy" (not containing amylose) wheat by cross-breeding of mutants occurring in nature (Nakamura et al., Mol. Gen. Genet. 248 (1995), 253–259). Another possibility is the specific genetic modification of the starch metabolism of starch-producing plants by means of recombinant DNA techniques. However, a prerequisite therefor is to identify and to characterize the enzymes involved in the starch synthesis and/or the starch modification as well as to isolate the respective DNA molecules encoding these enzymes. The biochemical pathways which lead to the production of starch are basically known. The starch synthesis in plant cells takes place in the plastids. In photosynthetically active tissues these are the chloroplasts, in photosynthetically inactive, starch-storing tissues the amyloplasts.

The most important enzymes involved in starch synthesis are starch synthases as well as branching enzymes. In the case of starch synthases various isotypes are described which all catalyze a polymerization reaction by transferring a glucosyl residue of ADP-glucose to α-1,4-glucans. Branching enzymes catalyze the introduction of α-1,6 branchings into linear α-1, 4-glucans.

Starch synthases may be divided up in two groups: the granule-bound starch synthases (GBSS) and the soluble starch synthases (SSS). This distinction is not always evident since some starch synthases are granule-bound as well as soluble (Denyer et al., Plant J. 4 (1993), 191–198; Mu et al., Plant J. 6 (1994), 151–159). Within these classifications, various isotypes are described for various species of plants. These isotypes differ from each other in their dependency on primer molecules (so-called "primer dependent" (type II) and "primer independent" (type I) starch synthases).

So far only in the case of the isotype GBSS I its exact function during starch synthesis has been successfully determined. Plants in which this enzyme activity has been strongly or completely reduced, synthesize starch free of amylose (a so-called "waxy" starch) (Shure et al., Cell 35 (1983), 225–233; Visser et al., Mol. Gen. Genet. 225 (1991), 289–296; WO 92/11376); therefore this enzyme has been assigned a decisive role in synthesizing amylose-starch. This phenomenon is also observed in the cells of the green alga Chlamydomonas reinhardtii (Delrue et al., J. Bacteriol. 174 (1992), 3612–3620). In the case of Chlamydomonas it was furthermore demonstrated that GBSS I is not only involved in the synthesis of amylose but also has an influence on amylopectin synthesis. In mutants which do not show any GBSS I activity a certain fraction of the normally synthesized amylopectin, exhibiting long chain glucans, is missing.

The functions of the other isotypes of the granule-bound starch synthases, particularly GBSS II, and of the soluble starch synthases are so far not clear. It is assumed that soluble starch synthases, together with branching enzymes, are involved in the synthesis of amylopectin (see e.g. Ponstein et al., Plant Physiol. 92 (1990), 234–241) and that they play an important role in the regulation of starch synthesis rate. In the case of wheat at least two isotypes of granule-bound starch synthase (60 kDa and 100–105 kDa) and a further isotype, which possibly represents a soluble starch synthase (Denyer et al., Planta 196 (1995), 256–265; Rahman et al., Aust. J. Plant Physiol. 22 (1995), 793–803), were identified on the protein level. The existence of several SSS-isotypes had already been proved by means of chromatographic methods (Rijven, Plant Physiol. 81 (1986), 448–453). A cDNA encoding GBSS I from wheat has already been described (Ainsworth et al., Plant Mol. Biol. 22 (1993), 67–82).

Nucleic acid sequences encoding further starch synthase-isotypes from wheat are yet unknown.

cDNA-sequences encoding other starch synthases than GBSS I have so far merely been described for pea (Dry et al., Plant J. 2 (1992), 193–202), rice (Baba et al., Plant Physiol. 103 (1993), 565–573) and potatoes (Edwards et al., Plant J. 8 (1995), 283–294).

Soluble starch synthases have been identified in several other plant species apart from wheat. Soluble starch synthases have for example been isolated in homogeneous form from pea (Denyer and Smith, Planta 186 (1992), 609–617) and potatoes (Edwards et al., Plant J. 8 (1995), 283–294). In these cases it was found that the isotype of the soluble starch synthase identified as SSS II is identical with the granule-bound starch synthase GBSS II (Denyer et al., Plant J. 4 (1993), 191–198; Edwards et al., Plant J. 8 (1995), 283–294). In the case of other plant species the existence of several SSS-isotypes was described by means of chromatographic methods, as for example in the case of barley (Tyynelä and Schulman, Physiologia Plantarum 89 (1993) 835–841; Kreis, Planta 148 (1980), 412–416). However, DNA sequences encoding these proteins have so far not been described.

In order to provide further possibilities for modifying any desired starch-storing plant, especially wheat, in such a way that they will synthesize a modified starch, respective DNA sequences encoding further isotypes of starch synthases have to be identified.

Therefore, it was the object of the present invention to provide nucleic acid molecules encoding enzymes—especially enzymes from wheat—involved in starch biosynthesis and by means of which genetically modified plants may be produced that show an elevated or reduced activity of those enzymes, thereby prompting a modification in the chemical and/or physical properties of the starch synthesized in these plants.

This object has been achieved by the provision of the embodiments described in the claims.

SUMMARY OF THE INVENTION

Therefore, in a first aspect the present invention relates to nucleic acid molecules encoding proteins from wheat with the biological activity of a soluble starch synthase, whereby such molecules preferably encode proteins which comprise the amino acid sequence depicted under Seq ID No. 2. The invention particularly relates to nucleic acid molecules which comprise all or part of the nucleotide sequence mentioned under Seq ID No. 1, preferably molecules, which comprise the coding region indicated in Seq ID No. 1 or, as the case may be, corresponding ribonucleotide sequences.

The present invention further relates to nucleic acid molecules encoding soluble starch synthase from wheat and hybridizing to one of the above-mentioned molecules.

Nucleic acid molecules that encode soluble starch synthase from wheat and the sequence of which differs from the nucleotide sequences of the above-mentioned molecules due to the degeneracy of the genetic code are also the subject-matter of the invention.

The invention also relates to nucleic acid molecules showing a sequence which is complementary to the whole or to a part of the above-mentioned sequences.

The proteins encoded by the above-described nucleic acid molecules are soluble starch synthases derived from wheat. These proteins show certain homologous regions with the so far known soluble starch synthases from other plant species.

In another aspect the present invention relates to nucleic acid molecules encoding proteins with the biological activity of a starch synthase from wheat, whereby such molecules preferably encode proteins comprising the amino acid sequence indicated under Seq ID No. 6. The invention particularly relates to nucleic acid molecules which contain the nucleotide sequence indicated under Seq ID No. 5 or part of it, preferably molecules comprising the coding region depicted under Seq ID No. 5 or, as the case may be, corresponding ribonucleotide sequences.

The present invention further relates to nucleic acid molecules encoding starch synthase from wheat and hybridizing to one of the above mentioned molecules.

Nucleic acid molecules that encode a starch synthase from wheat and the sequence of which differs from the nucleic acid sequences of the above-described molecules due to the degeneracy of the genetic code are also the subject-matter of the invention.

The invention also relates to nucleic acid molecules showing a sequence which is complementary to the whole or to a part of the above-mentioned sequences.

The protein encoded by the above-described nucleic acid molecules is a protein with the biological activity of a starch synthase from wheat. When comparing the homology with other known sequences it was found that the highest degree of homology occurs with peas, which encode a granule-bound starch synthase. Thus, it is assumed that the described nucleic acid molecules encode a granule bound starch synthase from wheat.

The nucleic acid molecules of the invention may be DNA as well as RNA molecules. Corresponding DNA molecules are for instance genomic or cDNA molecules. The nucleic acid molecules of the invention may be isolated from natural sources or synthesized by means of known methods.

In this invention the term "hybridization" signifies hybridization under conventional hybridizing conditions, preferably under stringent conditions as described for example in Sambrook et al., Molecular Cloning, A Laboratory Manual, 2nd Edition (1989) Cold Spring Harbor Laboratory Press, Cold Spring Harbor, N.Y.).

Nucleic acid molecules hybridizing to the molecules according to the invention may be isolated e.g. from genomic or from cDNA libraries produced from wheat tissue.

Thereby, the identification and isolation of such nucleic acid molecules may take place by using the molecules according to the invention or parts of these molecules or, as the case may be, the reverse complement strands of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequences indicated under Seq ID No. 1 or under Seq ID No. 5 or parts thereof. The fragments used as hybridization probe may also be synthetic fragments which were produced by means of the conventional synthesizing methods and the sequence of which is basically identical with that of a nucleic acid molecule according to the invention. After identifying and isolating the genes hybridizing to the nucleic acid sequences according to the invention, the sequence has to be determined and the properties of the proteins encoded by this sequence have to be analyzed.

The molecules hybridizing to the nucleic acid molecules of the invention also comprise fragments, derivatives and allelic variants of the above-described nucleic acid molecules which encode a protein from wheat as described in the invention. Thereby, fragments are defined as parts of the nucleic acid molecules, which are long enough in order to encode one of the described proteins. This includes also parts of nucleic acid molecules according to the invention which lack the nucleotide sequence encoding the signal peptide responsible for the translocation of the protein into the plastid. Such fragments are, for example, the nucleotide sequence encoding amino acid residues 34 to 671 as shown in Seq ID No. 2 or the nucleotide sequence encoding the amino acid residues 58 to 799 or 61 to 799 as shown in Seq ID No. 6. Furthermore, fragments which are particularly preferred in the present invention are the fragments comprising nucleotides 186 to 2239 of Seq ID No. 1 as well as fragments comprising an additional G residue at their 5'-end, and fragments comprising nucleotides 1084 to 2825 of Seq ID No. 2. In this context, the term derivatives means that the sequences of these molecules differ from the sequences of the above-mentioned nucleic acid molecules at one or more positions and that they exhibit a high degree of homology to these sequences. Hereby, homology means a sequence identity of at least 40%, in particular an identity of at least 60%, preferably of more than 80% and still more preferably a sequence identity of more than 90%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are homologous to the above-described molecules and represent derivatives of these molecules, are generally variations of these molecules, that constitute modifications which exert the same biological function. These variations may be naturally occurring variations, for example sequences derived from other organisms, or mutations, whereby these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability, pH-optimum, temperature-optimum etc. Significant characteristics of a starch synthase are: i) their localization within the stroma of the plastids of plant cells; ii) their capability of synthesizing linear α-1,4-linked polyglucans using ADP-glucose as substrate. This activity can be determined as shown in Denyer and Smith (Planta 186 (1992), 606–617) or as described in the examples.

Nucleic acid molecules hybridizing specifically to a strand of the nucleic acid molecules of the invention are also subject-matter of the invention. These are preferably oligonucleotides with a length of at least 10, particularly of at least 15 and still more preferably with a length of at least 50 nucleotides. These nucleic acid molecules hybridize specifically to a strand of a nucleic acid molecule of the invention, i.e. they do not or only to a small extent hybridize to nucleic acid sequences encoding other proteins, particularly other starch synthases. The oligonucleotides of the invention may be used for example as primer for a PCR reaction. They may also be components of antisense-constructs or DNA molecules encoding suitable ribozymes.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and synthesis of a translatable RNA in procaryotic or eucaryotic cells.

The expression of the nucleic acid molecules of the invention in procaryotic cells, e.g. in *Escherichia coli*, is interesting insofar as this enables a more precise characterization of the enzymatic activities of the enzymes encoding these molecules. In particular, it is possible to characterize the product being synthesized by the respective enzymes in the absence of other enzymes which are involved in the starch synthesis of the plant cell. This makes it possible to draw conclusions about the function, which the respective protein exerts during the starch synthesis within the plant cell.

Moreover, it is possible to introduce various mutations into the nucleic acid molecules of the invention by means of conventional molecular-biological techniques (see e.g. Sambrook et al., 1989, Molecular Cloning, A Laboratory Manual, 2nd Edition, Cold Spring Harbor Laboratory Press, Cold Spring Harbor, N.Y.), whereby the synthesis of proteins with possibly modified biological properties is induced. By means of this it is on the one hand possible to produce deletion mutants, in which nucleic acid molecules are produced by continuing deletions at the 5' - or the 3' -end of the encoding DNA-sequence. These nucleic acid molecules may lead to the synthesis of correspondingly shortened proteins. Such deletions at the 5'-end of the nucleotide sequence make it possible, for example, to identify amino acid sequences which are responsible for the translocation of the enzyme in the plastids (transit peptides). This allows for the specific production of enzymes which due to the removal of the respective sequences are no longer located in the plastids but within the cytosol, or which due to the addition of other signal sequences are located in other compartments.

On the other hand point mutations might also be introduced at positions where a modification of the amino acid sequence influences, for example, the enzyme activity or the regulation of the enzyme. In this way e.g. mutants with a modified $K_m$-value may be produced, or mutants which are no longer subject to the regulation mechanisms by allosteric regulation or covalent modification usually occurring in cells.

Furthermore, mutants may be produced exhibiting a modified substrate or product specificity such as mutants that use ADP-glucose-6-phosphate instead of ADP-glucose as substrate. Moreover, mutants with a modified activity-temperature-profile may be produced.

For the genetic manipulation in procaryotic cells the nucleic acid molecules of the invention or parts of these molecules may be integrated into plasmids which allow for a mutagenesis or a sequence modification by recombination of DNA sequences. By means of standard methods (cf. Sambrook et al., 1989, Molecular Cloning: A laboratory manual, 2nd edition, Cold Spring Harbor Laboratory Press, N.Y., USA) base exchanges may be carried out or natural or synthetic sequences may be added. In order to connect the DNA fragments, adapters or linkers may be attached to the fragments. Moreover, use can be made of manipulations which offer suitable restriction sites or which remove superfluous DNA or restriction sites. Wherever use is made of inserts, deletions or substitutions, in vitro mutagenesis, "primer repair", restriction or ligation may be used. For analyzing use is usually made of a sequence analysis, a restriction analysis and further biochemico-molecularbiological methods.

In a further embodiment the invention relates to host cells, in particular procaryotic or eucaryotic cells, which have been transformed and/or genetically modified by an abovementioned nucleic acid molecule of the invention or by a vector of the invention, as well as cells derived from cells transformed and/or genetically modified in such a way and containing a nucleic acid molecule of the invention or a vector of the invention. This is preferably a bacterial cell or a plant cell. Such cells are characterized in that the introduced nucleic acid molecule of the invention is either heterologous with respect to the transformed cell, i.e. it does not occur naturally in these cells, or is located at another place in the genome than the corresponding, naturally occurring sequence. Furthermore, the proteins encoded by the nucleic acid molecules of the invention are the subject-matter of the invention as well as methods for their production whereby a host cell of the invention is cultivated under conditions that allow for a synthesis of the protein and whereby the protein is then isolated from the cultivated cells and/or the culture medium.

Moreover, the present invention also relates to transgenic plant cells transformed with one or more nucleic acid molecule(s) of the invention. Such cells contain one or more nucleic acid molecule(s) of the invention, whereby this/these is/are preferably linked to regulatory DNA elements, wnich ensure the transcription in plant cells, especially with a promoter. Such cells differ from naturally occurring plant cells in that they contain at least one nucleic acid molecule of the invention which does not naturally occur in such cells or in that such a molecule is integrated at some position in the genome of the cell at which is does not naturally occur, i.e. in a different genomic environment.

By means of methods known to the skilled person the transgenic plant cells can be regenerated to whole plants. Thus, the plants obtained by regenerating the transgenic plant cells of the invention are also the subject-matter of the present invention. A further subject-matter of the invention are plants which contain the above-described transgenic plant cells. The transgenic plants may in principle be plants of any desired species, i.e. they may be monocotyledonous as well as dicotyledonous plants. These are preferably useful plants., in particular starch-synthesizing or starch-storing plants such as cereals (rye, barley, oats, wheat etc.), rice, maize, peas, cassava or potatoes.

By making available the nucleic acid molecules of the invention it is now possible—by means of recombinant DNA techniques—to specifically interfere with the starch metabolism of plants in a way so far impossible by means of breeding. Thereby, the starch metabolism may be modified in such a way that a modified starch is synthesized which e.g. is modified, compared to the starch synthesized in wildtype plants, with respect to its physico-chemical properties, especially the amylose/amylopectin ratio, the degree of branching, the average chain length, the phosphate content, the pastification behavior, the size and/or the shape of the starch granule. There is the possibility of increasing the yield of genetically modified plants by increasing the activity of the proteins described in the invention, e.g. by overexpressing the respective nucleic acid molecules or by making mutants available which are no longer subject to cell-specific regulation schemes and/or different temperature-dependencies with respect to their activity. The economic significance of the chance to interfere with the starch synthesis of wheat is obvious since this plant produces considerable amounts of starch.

Therefore it is possible to express the nucleic acid molecules of the invention in plant cells in order to increase the activity of the respective starch synthases or it is possible to introduce them into cells that usually do not express said enzyme. Furthermore, the nucleic acid molecules of the invention may be modified by means of methods known to the skilled person, in order to produce starch synthases according to the invention which are no longer subject to the cell-specific regulation mechanisms or show modified temperature-dependencies or substrate resp. product specificities.

In expressing the nucleic acid molecules of the invention in plants the synthesized proteins may in principle be located in any desired compartment within the plant cell. In order to locate it within a specific compartment, the sequence ensuring the localization in the plastids must be deleted and the remaining coding regions optionally have to be linked to DNA sequences which ensure localization in the respective compartment. Such sequences are known (see e.g. Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The invention also relates to propagation material of the plants of the invention, e.g. fruits, seeds, tubers, root-stocks, seedlings, cuttings, calli, cell cultures etc.

The starch derived from transgenic plant cells, plants as well as the propagation material according to the invention is also the subject-matter of the present invention.

Due to the expression or, as the case may be, additional expression of at least one of the nucleic acid molecules of the invention, the transgenic plant cells and plants described in the invention synthesize a starch which compared to starch synthesized in wildtype plants is modified for example in its physico-chemical properties, in particular in the amylose/amylopectin ratio, the degree of branching, the average chain-length, the phosphate-content, the pastification behavior, the size and/or the shape of the starch granule. Compared with wildtype-starch, such starch may be modified in particular with respect to its viscosity and/or the gel formation properties of the glues of this starch.

Transgenic plant cells, in which the activity of at least one protein according to the invention is reduced when compared to non-transformed plants, are a further subject-matter of the invention.

By means of the nucleic acid molecules of the invention it is possible to produce plant cells and plants in which the activity of at least one protein of the invention is reduced. This also leads to the synthesis of a starch with modified chemical and/or physical properties when compared to the starch from wildtype plant cells.

The production of plant cells with a reduced activity of at least one protein of the invention may, for example, be achieved by the expression of at least one corresponding antisense-RNA, of at least one sense-RNA for achieving a cosupression effect or the expression of at least one correspondingly constructed ribozyme, which specifically cleaves transcripts encoding one of the proteins of the invention, using the nucleic acid molecules of the invention.

In order to express an antisense-RNA, on the one hand DNA molecules can be used which comprise the complete sequence encoding a protein of the invention, including possibly existing flanking sequences as well as DNA molecules, which only comprise parts of the encoding sequence whereby these parts have to be long enough in order to prompt an antisense-effect within the cells. Basically, sequences with a minimum length of 15 bp, preferably with a length of 100–500 bp and for an efficient antisense-inhibition, in particular sequences with a length of more than 500 bp may be used. Generally DNA-molecules are used which are shorter than 5000 bp, preferably sequences with a length of less than 2500 bp.

Use may also be made of DNA sequences which are highly homologous, but not completely identical to the sequences of the DNA molecules of the invention. The minimal homology should be more than about 65%. Preferably, use should be made of sequences with homologies between 95 and 100%.

The method for reducing the activity of enzymes of the invention in plant cells by means of a cosuppression effect is known to the skilled person and has been described, for example, in Jorgensen (Trends Biotechnol. 8 (1990), 340–344), Niebel et al. (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al. (Mol. Gen. Genet. 248 (1995), 311–317), de Borne et al. (Mol. Gen. Genet. 243 (1994), 613–621) and in other sources.

The expression of corresponding ribozymes in order to reduce the activity of certain enzymes in cells is also known to the person skilled in the art and described, for example, in EP- B1 0 321 201. The expression of ribozymes in plant cells was described e.g. by Feyter et al. (Mol. Gen. Genet. 250 (1996), 329–338).

Moreover, plants containing the above-described transgenic plant cells of the invention are also the subject-matter of the present invention. These may be regenerated from the plant cells of the invention to whole plants by means of methods known to the skilled person. These plants are preferably those already mentioned above, in particular useful plants, especially starch-synthesizing or, as the case may be, starch-storing plants. Hereby, wheat is particularly preferred.

The invention also relates to propagation material of the plants of the invention, in particular to fruits, seeds, tubers, rootstocks, seedlings, cuttings, calli, cell cultures etc.

Moreover, starch derived from the above-mentioned transgenic plant cells, plants as well as the propagation material is the subject-matter of the invention.

Due to the reduction of the activity of at least one of the proteins of the invention, the transgenic plant cells and plants of the invention synthesize a starch which is modified, compared to the starch synthesized in wildtype plants, in its physico-chemical properties, in particular in the amylose/amylopectin ratio, the degree of branching, the average chain-length, the phosphate-content, the pastification behavior, the size and/or the shape of the starch granule. This starch may for example exhibit modified viscosities and/or gel formation properties of its glues when compared to starch derived from wildtype plants.

The starches of the invention may be modified according to techniques known to the skilled person; in unmodified as well as in modified form they are suitable for the use in foodstuffs or for the use in non-foodstuffs.

Basically, the possibilities of uses of the starch can be subdivided into two major fields. One field comprises the hydrolysis products of starch, essentially glucose and glucans components obtained by enzymatic or chemical processes. They can be used as starting material for further chemical modifications and processes, such as fermentation. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The other field in which the starch is used because of its polymer structure as so-called native starch, can be subdivided into two further areas:

1. Use in foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

A preferred area of application of native starch is the field of bakery-goods and pasta.

2. Use in non-foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles., as solidifying substance and for dehydration. In addition, the advantageous properties of starch with regard to stiffness, hardness, sound, grip, gloss, smoothness, tear strength as well as the surfaces are utilized.

2.1 Paper and cardboard industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and textile care industry

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building industry

The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral f fibers. In ready-mixed concrete, starch may be used for the deceleration of the sizing process.

2.5 Ground stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and incrustation-reducing effect as the products used so far; however, they are considerably less expensive.

2.6 Use of starch in plant protectives and fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, medicine and cosmetics industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an additive in coal and briquettes

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5w. Furthermore, the starch is suitable as a binding agent since adding it to coal and briquette can considerably reduce the emission of toxic substances.

2.9 Processing of ore and coal slurry

Furthermore, the starch may be used as a flocculant in the processing of ore and coal slurry.

2.10 Starch as an additive in casting

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Use of starch in rubber industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of leather substitutes

Another field of application for the modified starch is the production of leather substitutes.

2.13 Starch in synthetic polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes. Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment acid treatment oxidation and esterification leading to the formation of phosphate, nitrate, sulfate, xanthate, acetate and citrate starches. Other organic acids may also be used for the esterification:

formation of starch ethers starch alkyl ether, O-allyl ether, hydroxyalkyl ether, O-carbonylmethyl ether, N-containing starch ethers, p-containing starch ethers and S-containing starch ethers.

formation of branched starches formation of starch graft polymers.

The starches of the invention are preferably used in the production of packaging and disposable material.

In order to express the nucleic acid molecules of the invention in sense- or antisense-orientation in plant cells, these are linked to regulatory DNA elements which ensure the transcription in plant cells. Such regulatory DNA elements are particularly promoters. Basically any promoter which is active in plant cells may be used for the expression.

The promoter may be selected in such a way that the expression takes place constructively or in a certain tissue, at a certain point of time of the plant development or at a point of time determined by external circumstances. With respect to the plant the promoter may be homologous or heterologous. Suitable promoters for a constitutive expression are, e.g. the 35S RNA promoter of the Cauliflower Mosaic Virus and the ubiquitin promoter from maize. For a tuber-specific expression in potatoes the patatin gene promoter B33 (Rocha-Sosa et al., EMBO J. 8 (1989), 23–29) can be used. An example for a promoter which ensures expression only in photosynthetically active tissues is the ST-LS1 promoter (Stockhaus et al., Proc. Natl. Acad. Sci. USA 84 (1987), 7943–7947; Stockhaus et al., EMBO J. 8 (1989), 2445–2451). For an endosperm-specific expression the HMG promoter from wheat, the USP promoter, the phaseolin promoter or promoters from zein genes from maize are suitable. Furthermore, a termination sequence may exist which serves to correctly end the transcription and to add a poly-A-tail to the transcript which is believed to stabilize the transcripts. Such elements are described in the literature (cf. Gielen et al., EMBO J. 8 (1989), 23–29) and can be exchanged as desired.

The present invention provides nucleic acid molecules encoding two distinctive types of starch synthase from wheat. This allows for the identification of the function of these isotypes in the starch biosynthesis as well as for the production of genetically modified plants in which the activity of at least one of these enzymes is modified. This enables the synthesis of starch with a modified structure and therefore with modified physico-chemical properties in the plants manipulated in such a way.

The nucleic acid molecules of the invention may also be used in order to produce plants in which the activity of at least one of the starch synthases of the invention is elevated or reduced and in which at the same time the activities of other enzymes involved in the starch biosynthesis are modified. Thereby, all kinds of combinations and permutations are thinkable. By modifying the activity of one or more isotypes of the starch synthases in plants, a synthesis of a starch modified in its structure is brought about. By increasing the activity of one or more isotypes of the starch synthases in the cells of the starch-storing tissue of transformed plants such as in the endosperm of maize or wheat or in the potato tuber, increased yields may be the result. For example, nucleic acid molecules encoding a protein of the invention, or corresponding antisense-constructs may be integrated into plant cells in which the synthesis of endogenous GBSS I-, SSS- or GBSS II-proteins is already inhibited due to an antisense-effect or a mutation, or in which the synthesis of the branching enzyme is inhibited (as described e.g. in Nakamura et al. (loc. cit.)).

If the inhibition of the synthesis of several starch synthases in transformed plants is to be achieved, DNA molecules can be used for transformation, which at the same time contain several regions in antisense-orientation controlled by a suitable promoter and encoding the corresponding starch synthases. Hereby, each sequence may be controlled by its own promoter or else the sequences may be transcribed as a fusion of a common promoter. The last alternative will generally be preferred as in this case the synthesis of the respective proteins should be inhibited to approximately the same extent.

Furthermore it is possible to construct DNA molecules which, apart from DNA sequences that encode starch synthases, contain further DNA sequences encoding other proteins involved in starch synthesis or modification. Hereby, the sequences may again be connected up in series and be transcribed by a common promoter. For the length of the individual coding regions used in such a construct the above-mentioned facts concerning the production of antisense-construct are also true. There is no upper limit for the number of antisense fragments transcribed from a promoter in such a DNA molecule. The resulting transcript, however, should not be longer than 10 kb, preferably 5 kb.

Coding regions which are located in antisense-orientation behind a suitable promoter in such DNA molecules in combination with other coding regions, may be derived from DNA sequences encoding the following proteins: granule-bound starch synthases (GBSS I and II), other soluble starch synthases, branching enzymes, debranching enzymes, disproportionizing enzymes and starch phosphorylases. This enumeration merely serves as an example. The use of other DNA sequences within the framework of such a combination is also thinkable.

By means of such constructs it is possible to inhibit the synthesis of several enzymes at the same time within the plant cells transformed with these molecules.

Furthermore, the constructs may be integrated into classical mutants which are defective for one or more genes of the starch biosynthesis. These defects may be related to the following proteins: granule-bound (GBSS I and II) and soluble starch synthases (SSS I and II), branching enzymes (BE I and II) debranching enzymes (R-enzymes), disproportionizing enzymes and starch phosphorylases. This enumeration merely serves as an example.

By means of such strategy it is furthermore possible to inhibit the synthesis of several enzymes at the same time within the plant cells transformed with these nucleic acid molecules. In order to prepare the integration of foreign genes into higher plants a high number of cloning vectors are at disposal, containing a replication signal for *E.coli* and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of *E.coli* cells. Transformed *E.coli* cells are cultivated in a suitable medium and subsequently harvested and lysed. The plasmid is recovered. As an analyzing method for the characterization of the obtained plasmid DNA use is generally made of restriction analysis, gel electrophoresis and other biochemico-molecularbiological methods. After each manipulation the Dlasmid DNA may be cleaved and the obtained DNA fragments may be linked to other DNA sequences. Each plasmid DNA may be cloned into the same or in other plasmids. In order to integrate DNA into plant host cells a wide range of techniques are at disposal. These techniques comprise the transformation of plant cells with T-DNA by using Agrobacterium tumefaciens or Agrobacterium rhizogenes as transformation medium, the fusion of protoplasts, the injection and the electroporation of DNA, the integration of DNA by means of the biolistic method as well as further possibilities.

In the case of injection, the biolostic method and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of integrating desired genes into the plant cell, further DNA sequences may be necessary. If the Ti- or Ri-plasmid is used e.g. for the transformation of the plant cell, usually at least the right border, more frequently, however, the right and left border of the Ti- and Ri-plasmid T-DNA should be connected to the foreign gene to be integrated as a flanking region.

If Agrobacteria are used for the transformation, the DNA which is to be integrated should be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to Agrobacterium tumefaciens (conjugation). Binary vectors may replicate in *E.coli* as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is usually necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with Agrobacterium tumefaciens or Agrobacterium rhizogenes. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the integrated DNA is present or not. Other possibilities in order to integrate foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Puhler, P. Stadler, editors), Vol. 2, 627–659, VCH Weinheim-New York-Basel-Cambridge).

Alternative Systems for the transformation of monocotyledonous plants are the transformation by means of a biolistic approach, the electrically or chemically induced DNA integration in protoplasts, the electroporation of partially permeabilized cells, the macro-injection of DNA into inflorescences, the micro-injection of DNA into microspores and pro-embryos, the DNA integration by sprouting pollen and the DNA integration in embryos by swelling (review given in: Potrykus, Physiol. Plant (1990), 269–273).

Whereas the transformation of dicotyledonous plants by Ti-plasmid-vector systems by means of Agrobacterium tumefaciens is a well-established method, more recent studies indicate that the transformation with vectors based on Agrobacterium can also be used in the case of monocotyledonous plants (Chan et al., Plant Mol. Biol. 22 (1993), 491–506; Hiei et al., Plant J. 6 (1994), 271–282; Bytebier et al., Proc. Natl. Acad. Sci. USA 84 (1987), 5345–5349; Raineri et al., Bio/Technology 8 (1990), 33–38; Gould et al., Plant Physiol. 95 (1991), 426–434; Mooney et al., Plant, Cell Tiss. & Org. Cult. 25 (1991), 209–218; Li et al., Plant Mol. Biol. 20 (1992), 1037–1048).

Three of the above-mentioned transformation systems have in the past been established for various types of cereals: electroporation of plant tissue, transformation of protoplasts and the DNA-transfer by particle-bombardment in regenerative tissue and cells (review given in: Jähne et al., Euphytica 85 (1995), 35–44).

In the corresponding literature the transformation of wheat is described in various ways (reviewed in Maheshwari et al., Critical Reviews in Plant Science 14 (2) (1995), 149–178). Hess et al. (Plant Sci. 72 (1990), 233) used macroinjection in order to bring pollen and Agrobacteria close to each other. The mobilization of the plasmid containing the nptII gene as selectable marker was proved by means of the Southern blot analysis and the NPTII test. The transformants constituted a normal phenotype and were fertile. The kanamycin-resistence could be proved in two successive generations.

The first transgenic, fertile wheat plant that could be regenerated after its bombardment with microprojectile-bound DNA was described in Vasil et al. (Bio/Technology 10 (1992), 667–674). The target tissue for the bombardment was an embryogenic callus culture (type C callus). The bar gene, encoding a phosphinotricine phosphotransferase and therefore conveying a resistance against the herbicide phosphinotricine, was used as selectable marker gene.

A further system was described by Weeks et al. (Plant Physiol. 102 (1993), 1077–1084) as well as Becker et al. (Plant J. S(2) (1994), 299–307). Here the scutellum of immature embryos was used as target tissue for the DNA transformation. In an introductory in vitro phase the scutellum had been made to induce somatic embryos. The efficiency of the transformation is considerably higher in the system developed by Becker et al. (loc. cit.), with 1 transgenic plant per 83 embryos of the 'Florida' kind, than in the system established by Weeks et al., with 1 to 2 transgenic plants per 1000 embryos of the 'Bobwhite' kind.

The system developed by Becker et al. (loc. cit.) constitutes a basis for the transformation experiments described in the examples.

Once the introduced DNA has been integrated in the genome of the plant cell, it usually continues to be stable there and also remains within the descendants of the originally transformed cell. It usually contains a selectable marker which confers resistance against a biozide such as phosphinotricine or against an antibiotic such as kanamycin, G 418, bleomycin or hygromycin etc. to the transformed plant cells. The individually selected marker should therefore allow for a selection of transformed cells to cells lacking the integrated DNA.

The transformed cells grow in the usual way within the plants (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties. The plant cells produce seeds.

Two or more generations should be grown in order to ensure whether the phenotypic feature is kept stably and whether it is transferred. Furthermore, seeds should be harvested in order to ensure that the corresponding phenotype or other properties will remain.

DETAILED DESCRIPTION OF THE INVENTION

In the examples use is made of the following methods:
1. Cloning
    For cloning in *E.coli* the vector pBluescript II SK (Stratagene) was used.
2. Bacterial strains
    For the Bluescript vector and for the antisense-constructs use was made of the *E.coli* strain DH5α (Bethesda Research Laboratories, Gaithersburgh, USA). For the in vivo excision the *E.coli* strain XL1-Blue was used.
3. Transformation of immature wheat embryos
    Media used
    MS: 100 ml/l macrosalts
        1 mil/l microsalts
        2 ml/l Fe/NaEDTA
        30 g/l sucrose (D. Becker and H. Lörz, Plant Tissue Culture Manual (1996), B12: 1-20)
   #30: MS+2.4-D (2 mg/l)
   #31: MS+2.4-D (2 mg/l)+phosphinotricine (PPT, active component of the herbicide BASTA® (2 mg/l)
   #32: MS+2.4-D (0,1 mg/l)+PPT (2 mg/l)
   #39: MS+2.4-D (2 mg/ml) +each 0.5 M mannitose/sorbitol
   The indicated media were adjusted to a pH value of 5.6 with KOH and reinforced with 0.3% of Gelrite.
   The method for transforming immature embryos from wheat was developed and optimized by Becker and Lörz (D. Becker and H. Lörz, Plant Tissue Culture Manual (1996), B12: 1–20).
   In the experiments described in the following the protocol laid down by Becker and Lörz (loc. cit.) was observed.

For the transformation ears with caryopses in the developing stage of 12 to 14 days are harvested after anthesis and subjected to surface sterilization. The isolated scutella are plated with the embryo axis facing the medium on the induction medium #30.
   After 2–4 days of preculturing (26° C., dark) the explantates are transferred to medium #39 for osmotic pre-culturing (2–4 h, 26° C., dark).
   For biolistic transformation 29 μg of gold particles onto which 5 μg or 73 ng of the target-DNA have been precipitated are used for each shot. As the experiments carried out are co-transformations, the target-DNA is added to the precipitation mixture in a proportion of 1:1, consisting of the target gene and a resistence marker gene (bar-gene).

4. DIG-labelling of the DNA fragments
   The labelling of DNA fragments used as screening probes was achieved by a specific PCR by incorporating a DIG-labelled dUTP (Boehringer Mannheim, Germany).

EXAMPLE 1

Identification, isolation and characterization of a cDNA encoding soluble starch synthase from wheat (*Tricitum aestivum L.*, cv Florida)

The synthesis of cDNA resulted from poly(A)+-RNA of approximately 21 day-old wheat caryopses. All experiments mentioned in the following were carried out according to the protocol of the manufacturer (ZAP-CDNA Synthesis Kit and ZAP-cDNA Gigapack II Gold Cloning Kit, Stratagene GmbH, Heidelberg).

After determining the titers of the cDNA library a primary titer of 1.25×106 pfu/ml could be found. The screening was carried out by means of a DIG-labelled DNA fragment. Hereby, a DIG-labelled PCR fragment encoding a subfragment from the soluble starch synthase from rice (Baba et al., loc. cit.) was used as a probe. The primers used for the PCR had the sequence R₁:  ACA GGA TCC TGT GCT ATG CGG CGT GTG AAG      (Seq. ID No. 3)

R₂:  TTG GGA TCC GCA ATG CCC ACA GCA TTT TTT TC  (Seq. ID No. 4)

For screening approximately 5×10⁴ pfu per plate (15 cm in diameter) were plated. Positive clones were singled out. By means of in vivo excision singled-out clones were obtained as pBluescript SK(−) phagemides.

After analyzing the clones by means of mini preparations and after restriction of the plasmid-DNA the TaSSS clone was further processed.

EXAMPLE 2
Sequence analysis of the cDNA insert of the pTaSSS plasmid

The plasmid DNA of the clone TaSSS was isolated and the sequence of the cDNA insert was determined by means of the didesoxynuleotide-method (Sanger et al., Proc. Natl. Acad. Sci. USA 74 (1977), 5463–5467).

First, a partial sequence was determined comprising nucleotides 186 to 2239 as depicted in Seq ID No. 1 which contained an additional G residue at its 5'-end. The insert of the clone TaSSS has a length of 2239 bp and constitutes a nearly full-length cDNA. The nucleotide sequence is indicated under Seq ID No. 1. The corresponding amino acid sequence is indicated under Seq ID No. 2. A putative signal peptide cleavage site is located between amino acid residues 33 and 34 indicated in Seq ID No. 1.

A sequence analysis and a comparison with already published sequences showed that the sequence shown under Seq ID No. 1 is new and comprises a nearly full-length coding region which exhibits homologies to soluble starch synthases from other organisms. By means of the partial cDNA sequence of TaSSS it is possible for the person skilled in the field of molecular biology to isolate the missing region at the 5'-region and thereby to obtain a complete cDNA clone. In order to do so the 5'-region of the clone TaSSS may be used as probe for screening for the whole cDNA and a complete clone may be isolated using standard methods by means of hybridization. On the other hand the missing 5'-end may be obtained by using a 5'-Race-method (e.g. of Boehringer Mannheim or other manufacturers).

EXAMPLE 3
Producing the plant transformation vector pTaSSS-as

In order to express an antisense-RNA to the isolated cDNA from wheat a plant transformation vector was designed on the basis of pUC19 as base plasmid in which the cDNA insert of the plasmid pTaSSS is linked to a DNA fragment in antisense-orientation, whereby the expression is regulated by the ubiquitin-promoter. This promoter consists of the first untranslated exon and the first intron of the ubiquitini gene from maize (Christensen A. H. et al., Plant Molecular Biology 18 (1992), 675–689).

Parts of the polylinker and the NOS-terminator are obtained from the plasmid pAct1.cas (CAMBIA, TG 0063; Cambia, GPO Box 3200, Canberra ACT 2601, Australia). Vector constructs with this terminator and constructs based on pAct1.cas are described in McElroy et al. (Molecular Breeding 1 (1995), 27–37). For the transformation of wheat pTaSSS was used as described above.

EXAMPLE 4
Identification, isolation and characterization of another cDNA encoding starch synthase from wheat (Triticum aestivum L., cv Florida)

In a sequence comparison of the so far known sequences encoding soluble and granule-bound starch synthases from plants, it was obvious that there are three strongly conserved regions in between the various proteins.

In order to isolate soluble starch synthases from wheat, these three regions were selected in order to generate polyclonal peptide antibodies. Therefore three synthetic polypeptides with the following amino acid sequences were produced:

Peptide 1: NH₂-PWSKTGGLGDVC-COOH (SEQ ID NO: 7)

Peptide 2: NH₂-PSRFEPCGLNQLY-COOH (SEQ ID NO: 8)

Peptide 3: NH₂-GTGGLRDTVENC-COOH (SEQ ID NO: 9)

These peptides were coupled to a KLH carrier (keyhole limpet homocyanin) and subsequently used for the production of polyclonal antibodies in rabbits (Eurogentec, Seraing, Belgium).

The resulting antibodies were designated as follows:

anti-SS1 polyclonal antibody against peptide 1 anti-SS2 polyclonal antibody against peptide 2 anti-SS3 polyclonal antibody against peptide 3.

The antibodies were subsequently used in order to screen a cDNA library from wheat caryopses for sequences encoding starch synthases from wheat. For this purpose a cDNA expression library produced as described in example 1 was used. For the analysis of the phage plaques, these were transferred to nitro-cellulose filters which had previously been incubated in a 10 mM IPTG solution for 30–60 minutes and subsequently been dried on Whatman paper. The transfer took 3 h at 37° C. Afterwards the filter were incubated in a blocking solution for 30 min at room temperature and washed twice in TBST-puffer for 5–10 min; The filters were shaken with the polyclonal antibodies in a suitable dilution for 1 h at room temperature or for 16 h at 4° C. The identification of plaques expressing a protein which had been recognized by one of the antibodies was carried out by means of the Immun-Blot Assay Kit; Goat Anti-Rabbit IgG (Biorad) according to manufacturer's specification.

Phage clones of the cDNA library expressing a protein which had been recognized by one of the antibodies were further purified by using standard methods. By means of the in vivo excision-method (Strategene) E.coli-clones were produced from positive phage clones, which contained a doublestranded pBluescript II SK plasmid with the corresponding cDNA insert between the EcoRI and the XhoI site of the polylinker. After checking the size and the restriction pattern of the insert a suitable clone, TaSS1 was subjected to a sequence analysis.

EXAMPLE 5

Sequence analysis of the CDNA inserts of the pTaSS1 plasmid

The plasmid-DNA was isolated from the pTaSS1 clone and the sequence of the cDNA insert was determined by means of standard methods using the didesoxynucleotide method (Sanger et, al., Proc. Natl. Acad. Sci. USA 74 (1977), 5463–5467).

First, a partial sequence was determined comprising the nucleotides 1084 to 2825 as depicted in Seq ID No. 5.

The insert of the pTaSS1 clone has a length of 2825 bp and constitutes a complete cDNA. The nucleotide sequence is indicated under Seq ID No. 5. The corresponding amino acid sequence is indicated under Seq ID No. 6.

A sequence analysis and a comparison with already published sequences showed that the sequence indicated under Seq ID No. 5 is new and comprises a coding region exhibiting homologies to starch synthases from other organisms. It is assumed that this cDNA encodes a protein having the biological activity of a granule bound starch synthase.

Furthermore, due to homologies with known consensus sequences for signal peptide cleavage sites it had been found that the putative signal transit peptide is cleaved of between positions 57 and 58 or between positions 60 and 61 in the amino acid sequence as shown in Seq ID No. 6.

EXAMPLE 6

Production of the plant transformation vector pTaSS1 -as

In order to express a partial antisense-RNA to the isolated cDNA from wheat, a plant transformation vector was constructed on the basis of pUC19 as base plasmid. The plant transformation vector partially contains the cDNA insertion of the plasmid pTaSS1 in antisense-orientation. The expression is regulated by the ubiquitin-promoter. This promoter consists of the first untranslated exon and the first intron of the ubiquitini gene from maize (Christensen A. H. et al., Plant Molecular Biology 18 (1992), 675–689).

Parts of the polylinker and the NOS terminator are derived from the pAct.cas plasmid (CAMBIA, TG 0063; Cambia, GPO Box 3200, Canberra ACT 2601, Australia). Vector constructs with this terminator and constructs based on pAct1.cas are described in McElroy et al., (Molecular Breeding 1 (1995), 27–37).

In order to transform wheat the pTaSS1 -as vector is used as described above.

EXAMPLE 7

Complementation of an *E.coli* mutant with a cDNA clone encoding a wheat soluble starch synthase Enzymatic activity of the soluble starch synthase encoded by the cDNA clone TaSSS (Example 2) was analysed by complementation experiments using the *E. coli* mutant Hfr G6MD2 (M. Schwartz strain; CGSC #5080; E-coli Genetic Stock Center, New Haven, USA) as host for gene expression. The *E. coli* mutant shows a deletion of the glg-operon, encoding the bacterial ADP-glucose pyrophosphorylase (glg C), glycogen synthase (glg A) and branching enzyme (glg B). This mutation results in inability of glycogen synthesis through the ADP-glucose pathway. In addition, a deletion of the mal A operon prevents synthesis of linear α-1,4-glucans by the enzyme amylomaltase (mal Q).

The functionality of the soluble starch synthase was tested by cotransformation of the plasmids pTaSSSΔ188 and PACAG in the mutant G6MD2. The plasmid pTaSSSΔ188 comprise nucleotides 188–2239 of the 2239 bp cDNA sequence, which code for the soluble starch synthase. The cDNA is inserted as Eco RI/Xho I fragment in the polylinker region of the pBluescript vector (Stratagene). This allows the N-terminus of the α-peptide of the beta-galactosidase encoded by the vector to be fused in frame with a part of the soluble starch synthase.

A successful complementation of the glycogen synthase (glg A) mutation in G6MD2 is dependent on expression of an ADP-glucose pyrophosphorylase activity, responsible for supply of ADP-glucose, the substrat for synthesis of α-1,4-glucans. Therefore, the plasmid pACAG (Abel G. J. W., (1995), Untersuchungen zur Funktion von Stärke-Synthasen in der Kartoffel (*Solanum tuberosum L.*), Dissertation, Freie Universitat Berlin) comprising the coding region of the glg C locus isolated from the *E. coli* strain LCB 618 (Baecker et al., J. Biol. Chem, 258 (1983) 5084–5088) under control of the lacZ promoter was cotransformed. The encoded ADP-glucose pyrophosphorylase activity is less influenced by the activator fructose-1,6-bisphosphate and the inhibitor AMP resulting in sufficient supply of ADP-glucose.

Cells cotransformed with the constructs pTaSSSΔ188 and pACAG were plated out on LB-agar plates supplemented with 1% glucose, 1 mM IPTG and 50 µM diaminopimelate. The resulting colonies were stained by iodine steam. The transformed G6MD2 cells showed a blue-light brownish color in contrast to the yellowish color of untransformed colonies, which indicates the ADP glucose: α-1,4-D-glucan 4-α-glucosyltransferase activity of the expressed fusion protein.

The system was checked by iodine staining of G6MD2 cells cotransformed with the constructs pACAG and pEcS.3. The plasmid pEc5.3 comprises a glycogen synthase (glg A) gene isolated from the *E.coli* strain DHSA by PCR technologies (Abel G. J. W., (1995), Untersuchungen zur Funktion von Starke-Synthasen in der Kartoffel (*Solanum tuberosum L.*), Dissertation, Freie Universität Berlin). The transformed cells showed a dark blue color after staining with iodine, which indicates synthesis of α-1,4-glucans.

What is claimed is:

1. An isolated nucleic acid molecule comprising a nucleic acid sequence encoding a protein with a biological activity of a starch synthase, wherein the nucleic acid sequence is selected from the group consisting of:
   (a) a nucleic acid sequence encoding a protein comprising the amino acid sequence of SEQ ID NO:2;
   (b) a nucleic acid sequence comprising the coding region of SEQ ID NO: 1;
   (c) a nucleic acid sequence that has at least 60% sequence identity to the entire coding region of the nucleic acid sequence of (a) or (b) and that encodes a protein with a biological activity of a soluble starch synthase;
   (d) a nucleic acid sequence that deviates from the sequence of any one of the nucleic acid sequences of (a), (b) or (c) due to the degeneracy of the genetic code;
   (e) a nucleic acid sequence encoding a protein which comprises the amino acid sequence of SEQ ID NO:6
   (f) a nucleic acid sequence comprising the coding region of SEQ ID NO:5;
   (g) a nucleic acid sequence that has at least 60% sequence identity to the entire coding region of the nucleic acid sequence of (e) or (f) and that encodes a protein with a biological activity of a granule bound starch synthase; and
   (h) a nucleic acid sequence that deviates from the sequence of any one of the sequences of (e), (f), or (g) due to the degeneracy of the genetic code.

2. The nucleic acid molecule according to claim 1, wherein the molecule is a DNA molecule.

3. The DNA molecule according to claim 2, wherein the DNA molecule is a cDNA molecule.

4. The nucleic acid molecule according to claim 1, wherein the molecule is a RNA molecule.

5. A vector comprising the nucleic acid molecule according to any one of claim 1 to 4.

6. The vector according to claim 5 wherein the nucleic acid molecule is linked in sense-orientation to regulatory elements to ensure the transcription of a translatable RNA in procaryotic or eucaryotic cells.

7. A transgenic host cell comprising the nucleic acid molecule according to any one of claim 1 to 4 or a vector comprising the nucleic acid molecule, or a cell derived from said transgenic host cell and comprising said nucleic acid molecule or said vector.

8. A method for the production of starch synthase comprising the step of cultivating the host cell according to claim 7 under conditions that allow for the synthesis of the protein.

9. A transgenic plant cell comprising the nucleic acid molecule according to any one of claim 1 to 4 or a vector comprising the nucleic acid molecule, or a cell derived from said transgenic plant cell and comprising said nucleic acid molecule or said vector.

10. A plant comprising the plant cell according to claim 9.

11. The plant according to claim 10, wherein the plant is a starch-synthesizing and/or starch-storing plant.

12. The plant according to claim 11 wherein the plant is a starch-storing plant.

13. The plant according to claim 12, wherein the plant is selected from the group consisting of rye, barley, oats, wheat, rice, maize, peas, cassava and potatoes.

14. A propagation material of the plant according to claim 10.

15. An isolated nucleic acid molecule comprising a nucleotide sequence encoding a protein with a biological activity of a starch synthase, wherein the nucleic acid sequence is more than 90% homologous to:

(a) the coding region of SEQ ID NO: 1; or
(b) the coding region of SEQ ID NO:5.

16. The nucleic acid molecule according to claim 15, wherein the nucleotide sequence is the coding region of SEQ ID NO: 1 or the coding region of SEQ ID NO: 5.

17. A vector comprising the nucleic acid molecule according to claim 15 or 16.

18. A host cell comprising the nucleic acid molecule according to claim 15 or claim 16 or a vector comprising the nucleic acid molecule, or a cell derived from said transgenic host cell and comprising said nucleic acid molecule or said vector.

19. A method for the production of a starch synthase comprising the step of cultivating the host cell according to claim 18 under conditions that allow for the synthesis of the protein.

20. A transgenic plant cell comprising the nucleic acid molecule according to claim 15 or 16 or a vector comprising the nucleic acid molecule, or a cell derived from said transgenic plant cell and comprising said nucleic acid molecule or said vector.

21. A transgenic plant comprising the plant cell according to claim 20.

22. The transgenic plant according to claim 21, wherein the plant is a starch-storing plant.

23. The transgenic plant according to claim 21, wherein the plant is selected from the group consisting of rye, barley, oats, wheat, rice, maize, peas, cassava and potatoes.

24. A propagation material of the plant according to claim 21.

25. An isolated nucleic acid molecule comprising a nucleic acid sequence encoding a protein with a biological activity of a starch synthase, wherein the nucleic acid sequence has at least 60% sequence identity to:

(a) the entire coding region of SEQ ID NO: 1; or
(b) the entire coding region of SEQ ID NO: 5.

26. The nucleic acid molecule according to claim 1, wherein the nucleic acid sequence is a nucleic acid sequence encoding a protein comprising the amino acid sequence of SEQ ID NO: 2.

27. The nucleic acid molecule according to claim 1, wherein the nucleic acid sequence is a nucleic acid sequence encoding a protein which comprises the amino acid sequence of SEQ ID NO: 6.

28. The nucleic acid molecule according to claim 1, wherein the nucleic acid sequence is SEQ ID NO: 1 or SEQ ID NO: 5.

29. A transgenic host cell comprising the nucleic acid molecule according to any one of claim 25–28 or a vector comprising the nucleic acid molecule, or a cell derived from said transgenic host cell and comprising said nucleic acid molecule or said vector.

* * * * *

UNITED STATES PATENT AND TRADEMARK OFFICE
CERTIFICATE OF CORRECTION

PATENT NO. : 6,307,125 B1
DATED : October 23, 2001
INVENTOR(S) : Block et al.

It is certified that error appears in the above-identified patent and that said Letters Patent is hereby corrected as shown below:

Column 7,
Line 23, change "wnich" to -- which --.

Column 11,
Line 14, change "f fibers." to -- fibers. --.
Line 58, change "0.5w." to -- 0.5%. --.

Column 13,
Line 42, change "p-containing" to -- P-containing --.

Column 15,
Line 33, change "Dlasmid" to -- plasmid --.

Column 17,
Line 15, change "S (2)" to -- 5 (2) --.
Line 51, change "examples use" to -- examples, use --.

Column 18,
Line 7, change "+each" to -- + each --.
Lines 26 and 28, change "26° C" to -- 26°C --.
Lines 49-51, change "Identification, isolation and characterization of a cDNA encoding soluble starch synthase from wheat (*Tricitum aestivum L.*, cv Florida)" to -- Identification, isolation and characterization of a cDNA encoding soluble starch synthase from wheat (*Triticum aestivum L.*, cv Florida) --.
Line 53, change "poly (A) +-RNA" to -- poly (A) $^{+}$-RNA --.
Line 56, change "ZAP-CDNA" to -- ZAP-cDNA --.
Line 62, change "1.25x106" to -- $1.25 \times 10^6$ --.

Column 19,
Lines 16-17, change "Sequence analysis of the cDNA insert of the pTaSSS plasmid" to -- Sequence analysis of the cDNA insert of the pTaSSS plasmid --.

UNITED STATES PATENT AND TRADEMARK OFFICE
CERTIFICATE OF CORRECTION

PATENT NO. : 6,307,125 B1
DATED : October 23, 2001
INVENTOR(S) : Block et al.

It is certified that error appears in the above-identified patent and that said Letters Patent is hereby corrected as shown below:

Column 19,
Line 46, change "Producing the plant transformation vector pTaSSS-as" to
-- Producing the plant transformation vector pTaSSS-as --.
Lines 65-67, change "Identification, isolation and characterization of another cDNA encoding starch synthase from wheat (Triticum aestivum L., cv Florida)" to
-- Identification, isolation and characterization of another cDNA encoding starch synthase from wheat (*Triticum aestivum L.*, cv Florida) --.

Column 20,
Lines 60-61, change "Sequence analysis of the CDNA inserts of the pTaSS1 plasmid" to -- Sequence analysis of the cDNA inserts of the pTaSS1 plasmid --.

Column 21,
Line 20, change "Production of the plant transformation vector pTaSS1 -as" to
-- Production of the plant transformation vector pTaSS1 -as --.
Line 29, change "ubiquitini" to -- ubiquitin1 --.
Lines 41-42, change "Complementation of an *E. coli* mutant with a cDNA clone encoding a wheat soluble starch synthase" to -- Complementation of an *E. coli* mutant with a cDNA clone encoding a wheat soluble starch synthase --.
Line 46, change "CGSC #5080" to -- CGSC # 5080 --.
Line 48, change "glg-operon," to -- *glg-operon*, --.

Column 22,
Lines 1-3, change "(glg C), glycogen synthase (glg A) and branching enzyme (glg B)." to -- (*glg* C), glycogen synthase (*glg* A) and branching enzyme (*glg* B) --.
Line 5, change "mal A" to -- *mal A* --.
Line 6, change "(mal Q)" to -- (*mal* Q) --.
Line 12, change "EcoRI/XhoI" to -- *Eco*RI/*Xho*I --.
Lines 18 and 41, change "(glg A)" to -- (*glg* A) --.
Lines 23-24, change "*glg*" to -- *glg* --.
Line 27, change "lacZ" to -- *lacZ* --.
Line 40, change "pEcS.3." to -- pEc5.3. --.
Line 42, change "DHSA" to -- DH5α --.

UNITED STATES PATENT AND TRADEMARK OFFICE
CERTIFICATE OF CORRECTION

PATENT NO.     : 6,307,125 B1
DATED          : October 23, 2001
INVENTOR(S)    : Block et al.

It is certified that error appears in the above-identified patent and that said Letters Patent is hereby corrected as shown below:

<u>Column 45,</u>
Line 39, change "A host" to -- A transgenic host --.

Signed and Sealed this

Seventeenth Day of June, 2003

JAMES E. ROGAN
*Director of the United States Patent and Trademark Office*

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 2239 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO -continued

```
    (iv) ANTI-SENSE: NO (vi) ORIGINAL SOURCE:
         (A) ORGANISM: Triticum aestivum L.
         (B) STRAIN: cv. Florida
         (E) HAPLOTYPE: ca. 21 d Caryopses (vii) IMMEDIATE SOURCE:
         (A) LIBRARY: cDNA library in pBluescript sk (-)
         (B) CLONE: TaSSS (ix) FEATURE:
         (A) NAME/KEY: CDS
         (B) LOCATION:3..2017

(xi) SEQUENCE DESCRIPTION: SEQ ID NO: 1:
```

| | | | | | | | | | | | | | | | | |
|---|---|---|---|---|---|---|---|---|---|---|---|---|---|---|---|---|
| CG | ACG | CAG | CCG | CCC | CTG | CCG | GAC | GCC | GGC | GTG | GGG | GAA | CTC | GCG | CCC | 47 |
| | Thr | Gln | Pro | Pro | Leu | Pro | Asp | Ala | Gly | Val | Gly | Glu | Leu | Ala | Pro | |
| | 1 | | | 5 | | | | | 10 | | | | | 15 | | |
| GAC | CTC | CTG | CTC | GAA | GGG | ATT | GCT | GAG | GAT | TCC | ATC | GAC | AGC | ATA | ATT | 95 |
| Asp | Leu | Leu | Leu | Glu | Gly | Ile | Ala | Glu | Asp | Ser | Ile | Asp | Ser | Ile | Ile | |
| | | | 20 | | | | | 25 | | | | | 30 | | | |
| GTG | GCT | GCA | AGT | GAG | CAG | GAT | TCT | GAG | ATC | ATG | GAT | GCG | AAT | GAG | CAA | 143 |
| Val | Ala | Ala | Ser | Glu | Gln | Asp | Ser | Glu | Ile | Met | Asp | Ala | Asn | Glu | Gln | |
| | | | | 35 | | | | | 40 | | | | | 45 | | |
| CCT | CAA | GCT | AAA | GTT | ACA | CGT | AGC | ATC | GTG | TTT | GTG | ACT | GGT | GAA | GCT | 191 |
| Pro | Gln | Ala | Lys | Val | Thr | Arg | Ser | Ile | Val | Phe | Val | Thr | Gly | Glu | Ala | |
| | | | 50 | | | | | 55 | | | | | 60 | | | |
| GCT | CCT | TAT | GCA | AAG | TCA | GGG | GGG | TTG | GGA | GAT | GTT | TGT | GGT | TCG | TTA | 239 |
| Ala | Pro | Tyr | Ala | Lys | Ser | Gly | Gly | Leu | Gly | Asp | Val | Cys | Gly | Ser | Leu | |
| | 65 | | | | | 70 | | | | | 75 | | | | | |
| CCA | ATT | GCT | CTT | GCT | GCT | CGT | GGT | CAC | CGA | GTG | ATG | GTT | GTA | ATG | CCA | 287 |
| Pro | Ile | Ala | Leu | Ala | Ala | Arg | Gly | His | Arg | Val | Met | Val | Val | Met | Pro | |
| 80 | | | | | 85 | | | | | 90 | | | | | 95 | |
| AGA | TAC | TTA | AAT | GGG | TCC | TCT | GAT | AAA | AAC | TAT | GCA | AAG | GCA | TTA | TAC | 335 |
| Arg | Tyr | Leu | Asn | Gly | Ser | Ser | Asp | Lys | Asn | Tyr | Ala | Lys | Ala | Leu | Tyr | |
| | | | | 100 | | | | | 105 | | | | | 110 | | |
| ACT | GCG | AAG | CAC | ATT | AAG | ATT | CCA | TGC | TTT | GGG | GGA | TCA | CAT | GAA | GTG | 383 |
| Thr | Ala | Lys | His | Ile | Lys | Ile | Pro | Cys | Phe | Gly | Gly | Ser | His | Glu | Val | |
| | | | 115 | | | | | 120 | | | | | 125 | | | |
| ACC | TTT | TTT | CAT | GAG | TAT | AGA | GAC | AAC | GTC | GAT | TGG | GTG | TTT | GTC | GAT | 431 |
| Thr | Phe | Phe | His | Glu | Tyr | Arg | Asp | Asn | Val | Asp | Trp | Val | Phe | Val | Asp | |
| | | | 130 | | | | | 135 | | | | | 140 | | | |
| CAT | CCG | TCA | TAT | CAC | AGA | CCA | GGA | AGT | TTA | TAT | GGA | GAT | AAT | TTT | GGT | 479 |
| His | Pro | Ser | Tyr | His | Arg | Pro | Gly | Ser | Leu | Tyr | Gly | Asp | Asn | Phe | Gly | |
| | | | | 145 | | | | | 150 | | | | | 155 | | |
| GCT | TTT | GGT | GAT | AAT | CAG | TTC | AGA | TAC | ACA | CTC | CTT | TGC | TAT | GCT | GCA | 527 |
| Ala | Phe | Gly | Asp | Asn | Gln | Phe | Arg | Tyr | Thr | Leu | Leu | Cys | Tyr | Ala | Ala | |
| 160 | | | | | 165 | | | | | 170 | | | | | 175 | |
| TGC | GAG | GCC | CCA | CTA | ATC | CTT | GAA | TTG | GGA | GGA | TAT | ATT | TAT | GGA | CAG | 575 |
| Cys | Glu | Ala | Pro | Leu | Ile | Leu | Glu | Leu | Gly | Gly | Tyr | Ile | Tyr | Gly | Gln | |
| | | | | 180 | | | | | 185 | | | | | 190 | | |
| AAT | TGC | ATG | TTT | GTT | GTG | AAC | GAT | TGG | CAT | GCC | AGC | CTT | GTG | CCA | GTC | 623 |
| Asn | Cys | Met | Phe | Val | Val | Asn | Asp | Trp | His | Ala | Ser | Leu | Val | Pro | Val | |
| | | | 195 | | | | | 200 | | | | | 205 | | | |
| CTT | CTT | GCT | GCA | AAA | TAT | AGA | CCA | TAC | GGT | GTT | TAC | AGA | GAT | TCC | CGC | 671 |
| Leu | Leu | Ala | Ala | Lys | Tyr | Arg | Pro | Tyr | Gly | Val | Tyr | Arg | Asp | Ser | Arg | |
| | | | 210 | | | | | 215 | | | | | 220 | | | |
| AGC | ACC | CTT | GTT | ATA | CAT | AAT | TTA | GCA | CAT | CAG | GGT | GTG | GAG | CCT | GCA | 719 |
| Ser | Thr | Leu | Val | Ile | His | Asn | Leu | Ala | His | Gln | Gly | Val | Glu | Pro | Ala | |
| | | | | 225 | | | | | 230 | | | | | 235 | | |
| AGT | ACA | TAT | CCT | GAT | CTG | GGA | TTG | CCT | CCT | GAA | TGG | TAT | GGA | GCT | TTA | 767 |

-continued

```
Ser Thr Tyr Pro Asp Leu Gly Leu Pro Pro Glu Trp Tyr Gly Ala Leu
240                 245                 250                 255

GAA TGG GTA TTT CCA GAA TGG GCA AGG AGG CAT GCC CTT GAC AAG GGT      815
Glu Trp Val Phe Pro Glu Trp Ala Arg Arg His Ala Leu Asp Lys Gly
                    260                 265                 270

GAG GCA GTT AAC TTT TTG AAA GGA GCA GTT GTG ACA GCA GAT CGG ATT      863
Glu Ala Val Asn Phe Leu Lys Gly Ala Val Val Thr Ala Asp Arg Ile
                275                 280                 285

GTG ACC GTC AGT CAG GGT TAT TCA TGG GAG GTC ACA ACT GCT GAA GGT      911
Val Thr Val Ser Gln Gly Tyr Ser Trp Glu Val Thr Thr Ala Glu Gly
            290                 295                 300

GGA CAG GGC CTC AAT GAG CTC TTA AGC TCC CGA AAA AGT GTA TTG AAT      959
Gly Gln Gly Leu Asn Glu Leu Leu Ser Ser Arg Lys Ser Val Leu Asn
        305                 310                 315

GGA ATT GTA AAT GGA ATT GAC ATT AAT GAT TGG AAC CCC ACC ACA GAC     1007
Gly Ile Val Asn Gly Ile Asp Ile Asn Asp Trp Asn Pro Thr Thr Asp
320                 325                 330                 335

AAG TGT CTC CCT CAT CAT TAT TCT GTC GAT GAC CTC TCT GGA AAG GCC     1055
Lys Cys Leu Pro His His Tyr Ser Val Asp Asp Leu Ser Gly Lys Ala
                    340                 345                 350

AAA TGT AAA GCT GAA TTG CAG AAG GAG TTG GGT TTA CCT GTA AGG GAG     1103
Lys Cys Lys Ala Glu Leu Gln Lys Glu Leu Gly Leu Pro Val Arg Glu
                355                 360                 365

GAT GTT CCT CTG ATT GGC TTT ATT GGA AGA CTG GAT TAC CAG AAA GGC     1151
Asp Val Pro Leu Ile Gly Phe Ile Gly Arg Leu Asp Tyr Gln Lys Gly
            370                 375                 380

ATT GAT CTC ATT AAA ATG GCC ATT CCA GAG CTC ATG AGG GAG GAC GTG     1199
Ile Asp Leu Ile Lys Met Ala Ile Pro Glu Leu Met Arg Glu Asp Val
        385                 390                 395

CAA TTT GTC ATG CTT GGA TCT GGG GAT CCA ATT TTT GAA GGC TGG ATG     1247
Gln Phe Val Met Leu Gly Ser Gly Asp Pro Ile Phe Glu Gly Trp Met
400                 405                 410                 415

AGA TCT ACC GAG TCG AGT TAC AAG GAT AAA TTC CGT GGA TGG GTT GGA     1295
Arg Ser Thr Glu Ser Ser Tyr Lys Asp Lys Phe Arg Gly Trp Val Gly
                    420                 425                 430

TTT AGT GTT CCA GTT TCC CAC AGA ATA ACT GCA GGT TGC GAT ATA TTG     1343
Phe Ser Val Pro Val Ser His Arg Ile Thr Ala Gly Cys Asp Ile Leu
                435                 440                 445

TTA ATG CCA TCG AGA TTT GAA CCT TGC GGT CTT AAT CAG CTA TAT GCT     1391
Leu Met Pro Ser Arg Phe Glu Pro Cys Gly Leu Asn Gln Leu Tyr Ala
            450                 455                 460

ATG CAA TAT GGT ACA GTT CCT GTA GTT CAT GGA ACT GGG GGC CTC CGA     1439
Met Gln Tyr Gly Thr Val Pro Val Val His Gly Thr Gly Gly Leu Arg
        465                 470                 475

GAC ACA GTC GAG ACC TTC AAC CCT TTT GGT GCA AAA GGA GAG GAG GGT     1487
Asp Thr Val Glu Thr Phe Asn Pro Phe Gly Ala Lys Gly Glu Glu Gly
480                 485                 490                 495

ACA GGG TGG GCG TTC TCA CCG CTA ACC GTG GAC AAG ATG TTG TGG GCA     1535
Thr Gly Trp Ala Phe Ser Pro Leu Thr Val Asp Lys Met Leu Trp Ala
                    500                 505                 510

TTG CGA ACC GCG ATG TCG ACA TTC AGG GAG CAC AAG CCG TCC TGG GAG     1583
Leu Arg Thr Ala Met Ser Thr Phe Arg Glu His Lys Pro Ser Trp Glu
                515                 520                 525

GGG CTC ATG AAG CGA GGC ATG ACG AAA GAC CAT ACG TGG GAC CAT GCC     1631
Gly Leu Met Lys Arg Gly Met Thr Lys Asp His Thr Trp Asp His Ala
            530                 535                 540

CCG AGC AGT ACG AGC AGA TCT TCG AGT GGG CCT TCG TGG ACC AAC CCT     1679
Pro Ser Ser Thr Ser Arg Ser Ser Ser Gly Pro Ser Trp Thr Asn Pro
        545                 550                 555
```

-continued

```
ACG TCA TGT AGA CGG GGA CTG GGG AGG TCC AAG TGC GAG TCT CCT TCA      1727
Thr Ser Cys Arg Arg Gly Leu Gly Arg Ser Lys Cys Glu Ser Pro Ser
560                 565                 570                 575

GCT CTG AAG ACA TCC TCT TCA TCC TTC CGC GGC CCG GAA GGA TAC CCC      1775
Ala Leu Lys Thr Ser Ser Ser Phe Arg Gly Pro Glu Gly Tyr Pro
                580                 585                 590

TGT ACA TTG CGT TGT CCT GCT ACA GTA GAG TCG CAA TGC GCC TGC TTG      1823
Cys Thr Leu Arg Cys Pro Ala Thr Val Glu Ser Gln Cys Ala Cys Leu
        595                 600                 605

CTT TGG TTC GCC GGT TCG AGA ACA TAT GAC GGC TGT GCT GCT GCG GCG      1871
Leu Trp Phe Ala Gly Ser Arg Thr Tyr Asp Gly Cys Ala Ala Ala Ala
            610                 615                 620

GTG ACA GCT TCG GGT GGA CGA CAG TTA CAG TTT TGG GGA ATA AGG AAG      1919
Val Thr Ala Ser Gly Gly Arg Gln Leu Gln Phe Trp Gly Ile Arg Lys
625                 630                 635

GGA TGT GCT GCA GGA TGG TTA ACA GCA AAG CAC CAC TCA GAT GGC AGC      1967
Gly Cys Ala Ala Gly Trp Leu Thr Ala Lys His His Ser Asp Gly Ser
640                 645                 650                 655

CTC TCT GTC CGT GTT ACA GCT GAA ATC AGA AAC CAA CTG GTG ACT CTT TA   2017
Leu Ser Val Arg Val Thr Ala Glu Ile Arg Asn Gln Leu Val Thr Leu
                660                 665                 670

GCCTTAGTGA TTGTGAAGTT TGTTGCCTTC TGTGTATGTT GTCTTGTCCT TAGCTGACAA    2077

ATATTTGACC TGTTGGAGAA TTTTATCTTT GCTGCTGTTT TTTTTTAATC AAAAGAGGGG    2137

GTTTCCTCCG ATTTCATTAA AAAAAAAAAA AAAAAAAAAA AAAAAAAAAA AAAAAAAAAA    2197

AAAAAAAAAA AAAAAAAAAA AAAAAAAAAA AAAAAAAAAA AA                      2239

(2) INFORMATION FOR SEQ ID NO: 2:

(i) SEQUENCE CHARACTERISTICS:
        (A) LENGTH: 671 amino acids
        (B) TYPE: amino acid
        (D) TOPOLOGY: linear (ii) MOLECULE TYPE: protein (xi) SEQUENCE DESCRIPTION: SEQ ID NO: 2:

Thr Gln Pro Pro Leu Pro Asp Ala Gly Val Gly Glu Leu Ala Pro Asp
1               5                   10                  15

Leu Leu Glu Gly Ile Ala Glu Asp Ser Ile Asp Ser Ile Val
            20                  25                  30

Ala Ala Ser Glu Gln Asp Ser Glu Ile Met Asp Ala Asn Glu Gln Pro
        35                  40                  45

Gln Ala Lys Val Thr Arg Ser Ile Val Phe Val Thr Gly Glu Ala Ala
    50                  55                  60

Pro Tyr Ala Lys Ser Gly Gly Leu Gly Asp Val Cys Gly Ser Leu Pro
65                  70                  75                  80

Ile Ala Leu Ala Ala Arg Gly His Arg Val Met Val Met Pro Arg
                85                  90                  95

Tyr Leu Asn Gly Ser Ser Asp Lys Asn Tyr Ala Lys Ala Leu Tyr Thr
                100                 105                 110

Ala Lys His Ile Lys Ile Pro Cys Phe Gly Gly Ser His Glu Val Thr
        115                 120                 125

Phe Phe His Glu Tyr Arg Asp Asn Val Asp Trp Val Phe Val Asp His
        130                 135                 140

Pro Ser Tyr His Arg Pro Gly Ser Leu Tyr Gly Asp Asn Phe Gly Ala
145                 150                 155                 160

Phe Gly Asp Asn Gln Phe Arg Tyr Thr Leu Leu Cys Tyr Ala Ala Cys
```

-continued

```
                165                 170                 175
Glu Ala Pro Leu Ile Leu Glu Leu Gly Gly Tyr Ile Tyr Gly Gln Asn
            180                 185                 190
Cys Met Phe Val Val Asn Asp Trp His Ala Ser Leu Val Pro Val Leu
            195                 200                 205
Leu Ala Ala Lys Tyr Arg Pro Tyr Gly Val Tyr Arg Asp Ser Arg Ser
            210                 215                 220
Thr Leu Val Ile His Asn Leu Ala His Gln Gly Val Glu Pro Ala Ser
225                 230                 235                 240
Thr Tyr Pro Asp Leu Gly Leu Pro Pro Glu Trp Tyr Gly Ala Leu Glu
            245                 250                 255
Trp Val Phe Pro Glu Trp Ala Arg Arg His Ala Leu Asp Lys Gly Glu
            260                 265                 270
Ala Val Asn Phe Leu Lys Gly Ala Val Val Thr Ala Asp Arg Ile Val
            275                 280                 285
Thr Val Ser Gln Gly Tyr Ser Trp Glu Val Thr Thr Ala Glu Gly Gly
            290                 295                 300
Gln Gly Leu Asn Glu Leu Leu Ser Ser Arg Lys Ser Val Leu Asn Gly
305                 310                 315                 320
Ile Val Asn Gly Ile Asp Ile Asn Asp Trp Asn Pro Thr Thr Asp Lys
            325                 330                 335
Cys Leu Pro His His Tyr Ser Val Asp Asp Leu Ser Gly Lys Ala Lys
            340                 345                 350
Cys Lys Ala Glu Leu Gln Lys Glu Leu Gly Leu Pro Val Arg Glu Asp
            355                 360                 365
Val Pro Leu Ile Gly Phe Ile Gly Arg Leu Asp Tyr Gln Lys Gly Ile
            370                 375                 380
Asp Leu Ile Lys Met Ala Ile Pro Glu Leu Met Arg Glu Asp Val Gln
385                 390                 395                 400
Phe Val Met Leu Gly Ser Gly Asp Pro Ile Phe Glu Gly Trp Met Arg
            405                 410                 415
Ser Thr Glu Ser Ser Tyr Lys Asp Lys Phe Arg Gly Trp Val Gly Phe
            420                 425                 430
Ser Val Pro Val Ser His Arg Ile Thr Ala Gly Cys Asp Ile Leu Leu
            435                 440                 445
Met Pro Ser Arg Phe Glu Pro Cys Gly Leu Asn Gln Leu Tyr Ala Met
            450                 455                 460
Gln Tyr Gly Thr Val Pro Val Val His Gly Thr Gly Gly Leu Arg Asp
465                 470                 475                 480
Thr Val Glu Thr Phe Asn Pro Phe Gly Ala Lys Gly Glu Glu Gly Thr
            485                 490                 495
Gly Trp Ala Phe Ser Pro Leu Thr Val Asp Lys Met Leu Trp Ala Leu
            500                 505                 510
Arg Thr Ala Met Ser Thr Phe Arg Glu His Lys Pro Ser Trp Glu Gly
            515                 520                 525
Leu Met Lys Arg Gly Met Thr Lys Asp His Thr Trp Asp His Ala Pro
            530                 535                 540
Ser Ser Thr Ser Arg Ser Ser Gly Pro Ser Trp Thr Asn Pro Thr
545                 550                 555                 560
Ser Cys Arg Arg Gly Leu Gly Arg Ser Lys Cys Glu Ser Pro Ser Ala
            565                 570                 575
Leu Lys Thr Ser Ser Ser Phe Arg Gly Pro Glu Gly Tyr Pro Cys
            580                 585                 590
```

```
Thr Leu Arg Cys Pro Ala Thr Val Glu Ser Gln Cys Ala Cys Leu Leu
        595                 600                 605

Trp Phe Ala Gly Ser Arg Thr Tyr Asp Gly Cys Ala Ala Ala Val
        610                 615                 620

Thr Ala Ser Gly Gly Arg Gln Leu Gln Phe Trp Gly Ile Arg Lys Gly
625                 630                 635                 640

Cys Ala Ala Gly Trp Leu Thr Ala Lys His His Ser Asp Gly Ser Leu
                    645                 650                 655

Ser Val Arg Val Thr Ala Glu Ile Arg Asn Gln Leu Val Thr Leu
            660                 665                 670
```

(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: YES (xi) SEQUENCE DESCRIPTION: SEQ ID NO: 3:

ACAGGATCCT GTGCTATGCG GCGTGTGAAG                                    30

(2) INFORMATION FOR SEQ ID NO: 4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: YES (iv) ANTI-SENSE: NO (xi) SEQUENCE DESCRIPTION: SEQ ID NO: 4:

TTGGGATCCG CAATGCCCAC AGCATTTTTT TC                                 32

(2) INFORMATION FOR SEQ ID NO: 5:

(i) SEQUENCE CHARACTERISTICS:
        (A) LENGTH: 2825 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Triticum aestivum L.
        (B) STRAIN: cv. Florida
        (F) TISSUE TYPE: ca. 21 d Caryopses (vii) IMMEDIATE SOURCE:
        (A) LIBRARY: cDNA library in pBluescript sk (−)
        (B) CLONE: pTASS1

(ix) FEATURE:

(A) NAME/KEY: CDS
(B) LOCATION:162..2559

(xi) SEQUENCE DESCRIPTION: SEQ ID NO: 5:

```
CTTCGGCCTG ACCCCGTTCG TTTACCCCCA CACAGAGCAC ACTCCAGTCC AGTCCAGCCC      60

ACTGCCACCG CGCTACTCTC CACTCCCACT GCCACCACCT CCGCCTGCGC CGCGCTCTGG     120

GCGGACCAAC CCGCGAACCG TACCATCTCC CGCCCCGATC C ATG TCG TCG GCG        173
                                              Met Ser Ser Ala
                                                           675
```

| | | | | | | | | | | | | | |
|---|---|---|---|---|---|---|---|---|---|---|---|---|---|
| GTC | GCG | TCC | GCC | GCA | TCC | TTC | CTC | GCG | CTC | GCG | TCA | GCC | TCC | CCC | GGG | 221
| Val | Ala | Ser | Ala | Ala | Ser | Phe | Leu | Ala | Leu | Ala | Ser | Ala | Ser | Pro | Gly |
| | | | 680 | | | | 685 | | | | 690 | | | | |

```
GTC GCG TCC GCC GCA TCC TTC CTC GCG CTC GCG TCA GCC TCC CCC GGG      221
Val Ala Ser Ala Ala Ser Phe Leu Ala Leu Ala Ser Ala Ser Pro Gly
            680             685             690

AGA TCA CGC AGG CGG GCG AGG GTG AGC GCG CAG CCA CCC CAC GCC GGG      269
Arg Ser Arg Arg Arg Ala Arg Val Ser Ala Gln Pro Pro His Ala Gly
            695             700             705

GCC GGC AGG TTG CAC TGG CCG CCG TGG CCG CCG CAG CGC ACG GCT CGC      317
Ala Gly Arg Leu His Trp Pro Pro Trp Pro Pro Gln Arg Thr Ala Arg
            710             715             720

GAC GGA GCT GTG GCG GCG CTC GCC GCC GGG AAG AAG GAC GCG GGG ATC      365
Asp Gly Ala Val Ala Ala Leu Ala Ala Gly Lys Lys Asp Ala Gly Ile
725             730             735

GAC GAC GCC GCC GCG TCC GTG AGG CAG CCC CGC GCA CTC CGC GGT GGC      413
Asp Asp Ala Ala Ala Ser Val Arg Gln Pro Arg Ala Leu Arg Gly Gly
740             745             750             755

GCC GCC ACC AAG GTC GCG GAG CGA AGG GAT CCC GTC AAG ACG CTC GAC      461
Ala Ala Thr Lys Val Ala Glu Arg Arg Asp Pro Val Lys Thr Leu Asp
            760             765             770

CGC GAC GCC GCG GAA GGC GGC GGG CCG TCC CCG CCG GCA GCG AGG CAG      509
Arg Asp Ala Ala Glu Gly Gly Gly Pro Ser Pro Pro Ala Ala Arg Gln
            775             780             785

GAC GCC GCC CGT CCG CCG AGT ATG AAC GGC ATG CCG GTG AAC GGC GAG      557
Asp Ala Ala Arg Pro Pro Ser Met Asn Gly Met Pro Val Asn Gly Glu
            790             795             800

AAC AAA TCT ACC GGC GGC GGC GGC GCG ACT AAA GAC AGC GGG CTG CCC      605
Asn Lys Ser Thr Gly Gly Gly Gly Ala Thr Lys Asp Ser Gly Leu Pro
            805             810             815

ACG CCC GCA CGC GCG CCC CAT CCG TCG ACC CAG AAC AGA GCA CCG GTG      653
Thr Pro Ala Arg Ala Pro His Pro Ser Thr Gln Asn Arg Ala Pro Val
820             825             830             835

AAC GGT GAA AAC AAA GCT AAC GTC GCC TCG CCG CCG ACG AGC ATA GCC      701
Asn Gly Glu Asn Lys Ala Asn Val Ala Ser Pro Pro Thr Ser Ile Ala
            840             845             850

GAG GCC GCG GCT TCG GAT TCC GCA GCT ACC ATT TCC ATC AGC GAC AAG      749
Glu Ala Ala Ala Ser Asp Ser Ala Ala Thr Ile Ser Ile Ser Asp Lys
            855             860             865

GCG CCG GAG TCC GTT GTC CCA GCT GAG AAG ACG CCG CCG TCG TCC GGC      797
Ala Pro Glu Ser Val Val Pro Ala Glu Lys Thr Pro Pro Ser Ser Gly
            870             875             880

TCA AAT TTC GAG TCC TCG GCC TCT GCT CCC GGG TCT GAC ACT GTC AGC      845
Ser Asn Phe Glu Ser Ser Ala Ser Ala Pro Gly Ser Asp Thr Val Ser
            885             890             895

GAC GTG GAA CAA GAA CTG AAG AAG GGT GCG GTC GTT GTC GAA GAA GCT      893
Asp Val Glu Gln Glu Leu Lys Lys Gly Ala Val Val Val Glu Glu Ala
900             905             910             915

CCA AAG CCA AAG GCT CTT TCG CCG CCT GCA GCC CCC GCT GTA CAA GAA      941
Pro Lys Pro Lys Ala Leu Ser Pro Pro Ala Ala Pro Ala Val Gln Glu
            920             925             930

GAC CTT TGG GAT TTC AAG AAA TAC ATT GGT TTC GAG GAG CCC GTG GAG      989
Asp Leu Trp Asp Phe Lys Lys Tyr Ile Gly Phe Glu Glu Pro Val Glu
```

```
                    935                 940                 945
GCC AAG GAT GAT GGC CGG GCT GTC GCA GAT GAT GCG GGC TCC TTT GAA    1037
Ala Lys Asp Asp Gly Arg Ala Val Ala Asp Asp Ala Gly Ser Phe Glu
            950                 955                 960

CAC CAC CAG AAT CAC GAC TCC GGA CCT TTG GCA GGG GAG AAT GTC ATG    1085
His His Gln Asn His Asp Ser Gly Pro Leu Ala Gly Glu Asn Val Met
        965                 970                 975

AAC GTG GTC GTC GTG GCT GCT GAG TGT TCT CCC TGG TGC AAA ACA GGT    1133
Asn Val Val Val Val Ala Ala Glu Cys Ser Pro Trp Cys Lys Thr Gly
980                 985                 990                 995

GGT CTG GGA GAT GTT GCG GGT GCT CTG CCC AAG GCT TTG GCA AAG AGA    1181
Gly Leu Gly Asp Val Ala Gly Ala Leu Pro Lys Ala Leu Ala Lys Arg
                1000                1005                1010

GGA CAT CGT GTT ATG GTT GTG GTA CCA AGG TAT GGG GAC TAT GAA GAA    1229
Gly His Arg Val Met Val Val Val Pro Arg Tyr Gly Asp Tyr Glu Glu
            1015                1020                1025

GCC TAC GAT GTC GGA GTC CGA AAA TAC TAC AAG GCT GCT GGA CAG GAT    1277
Ala Tyr Asp Val Gly Val Arg Lys Tyr Tyr Lys Ala Ala Gly Gln Asp
            1030                1035                1040

ATG GAA GTG AAT TAT TTC CAT GCT TAT ATC GAT GGA GTT GAT TTT GTG    1325
Met Glu Val Asn Tyr Phe His Ala Tyr Ile Asp Gly Val Asp Phe Val
            1045                1050                1055

TTC ATT GAC GCT CCT CTC TTC CGA CAC CGT CAG GAA GAC ATT TAT GGG    1373
Phe Ile Asp Ala Pro Leu Phe Arg His Arg Gln Glu Asp Ile Tyr Gly
1060                1065                1070                1075

GGC AGC AGA CAG GAA ATT ATG AAG CGC ATG ATT TTG TTC TGC AAG GCC    1421
Gly Ser Arg Gln Glu Ile Met Lys Arg Met Ile Leu Phe Cys Lys Ala
                1080                1085                1090

GCT GTT GAG GTT CCA TGG CAC GTT CCA TGC GGC GGT GTC CCT TAT GGG    1469
Ala Val Glu Val Pro Trp His Val Pro Cys Gly Gly Val Pro Tyr Gly
            1095                1100                1105

GAT GGA AAT CTG GTG TTT ATT GCA AAT GAT TGG CAC ACG GCA CTC CTG    1517
Asp Gly Asn Leu Val Phe Ile Ala Asn Asp Trp His Thr Ala Leu Leu
            1110                1115                1120

CCT GTC TAT CTG AAA GCA TAT TAC AGG GAC CAT GGT TTG ATG CAG TAC    1565
Pro Val Tyr Leu Lys Ala Tyr Tyr Arg Asp His Gly Leu Met Gln Tyr
            1125                1130                1135

ACT CGG TCC ATT ATG GTG ATA CAT AAC ATC GCT CAC CAG GGC CGT GGC    1613
Thr Arg Ser Ile Met Val Ile His Asn Ile Ala His Gln Gly Arg Gly
1140                1145                1150                1155

CCT GTA GAT GAA TTC CCG TTC ACC GAG TTG CCT GAG CAC TAC CTG GAA    1661
Pro Val Asp Glu Phe Pro Phe Thr Glu Leu Pro Glu His Tyr Leu Glu
                1160                1165                1170

CAC TTC AGA CTG TAC GAC CCC GTG GGT GGT GAA CAC GCC AAC TAC TTC    1709
His Phe Arg Leu Tyr Asp Pro Val Gly Gly Glu His Ala Asn Tyr Phe
            1175                1180                1185

GCC GCC GGC CTG AAG ATG GCG GAC CAG GTT GTC GTG GTG AGC CCC GGG    1757
Ala Ala Gly Leu Lys Met Ala Asp Gln Val Val Val Val Ser Pro Gly
            1190                1195                1200

TAC CTG TGG GAG CTG AAG ACG GTG GAG GGC GGC TGG GGG CTT CAC GAC    1805
Tyr Leu Trp Glu Leu Lys Thr Val Glu Gly Gly Trp Gly Leu His Asp
            1205                1210                1215

ATC ATA CGG CAG AAC GAC TGG AAG ACC CGC GGC ATC GTC AAC GGC ATC    1853
Ile Ile Arg Gln Asn Asp Trp Lys Thr Arg Gly Ile Val Asn Gly Ile
1220                1225                1230                1235

GAC AAC ATG GAG TGG AAC CCC GAG GTG GAC GCC CAC CTC AAG TCG GAC    1901
Asp Asn Met Glu Trp Asn Pro Glu Val Asp Ala His Leu Lys Ser Asp
                1240                1245                1250

GGC TAC ACC AAC TTC TCC CTG AGG ACG CTG GAC TCC GGC AAG CGG CAG    1949
```

```
Gly Tyr Thr Asn Phe Ser Leu Arg Thr Leu Asp Ser Gly Lys Arg Gln
            1255                1260                1265

TGC AAG GAG GCC CTG CAG CGC GAG CTG GGC CTG CAG GTC CGC GCC GAC      1997
Cys Lys Glu Ala Leu Gln Arg Glu Leu Gly Leu Gln Val Arg Ala Asp
        1270                1275                1280

GTG CCG CTG CTC GGC TTC ATC GGC CGC CTG GAC GGG CAG AAG GGC GTG      2045
Val Pro Leu Leu Gly Phe Ile Gly Arg Leu Asp Gly Gln Lys Gly Val
    1285                1290                1295

GAG ATC ATC GCG GAC GCC ATG CCC TGG ATC GTG AGC CAG GAC GTG CAG      2093
Glu Ile Ile Ala Asp Ala Met Pro Trp Ile Val Ser Gln Asp Val Gln
1300                1305                1310                1315

CTG GTG ATG CTG GGC ACC GGG CGC CAC GAC CTG GAG AGC ATG CTG CAG      2141
Leu Val Met Leu Gly Thr Gly Arg His Asp Leu Glu Ser Met Leu Gln
            1320                1325                1330

CAC TTC GAG CGG GAG CAC CAC GAC AAG GTG CGC GGG TGG GTG GGG TTC      2189
His Phe Glu Arg Glu His His Asp Lys Val Arg Gly Trp Val Gly Phe
        1335                1340                1345

TCC GTG CGC CTG GCG CAC CGG ATC ACG GCG GGG GCG GAC GCG CTC CTC      2237
Ser Val Arg Leu Ala His Arg Ile Thr Ala Gly Ala Asp Ala Leu Leu
    1350                1355                1360

ATG CCC TCC CGG TTC GAG CCG TGC GGG CTG AAC CAG CTC TAC GCC ATG      2285
Met Pro Ser Arg Phe Glu Pro Cys Gly Leu Asn Gln Leu Tyr Ala Met
1365                1370                1375

GCC TAC GGC ACC GTC CCC GTC GTG CAC GCC GTC GGC GGC CTC AGG GAC      2333
Ala Tyr Gly Thr Val Pro Val Val His Ala Val Gly Gly Leu Arg Asp
1380                1385                1390                1395

ACC GTG CCG CCG TTC GAC CCC TTC AAC CAC TCC GGG CTC GGG TGG ACG      2381
Thr Val Pro Pro Phe Asp Pro Phe Asn His Ser Gly Leu Gly Trp Thr
            1400                1405                1410

TTC GAC CGC GCC GAG GCG CAC AAG CTG ATC GAG GCG CTC GGG CAC TGC      2429
Phe Asp Arg Ala Glu Ala His Lys Leu Ile Glu Ala Leu Gly His Cys
        1415                1420                1425

CTC CGC ACC TAC CGA GAC TTC AAG GAG AGC TGG AGG GCC CTC CAG GAG      2477
Leu Arg Thr Tyr Arg Asp Phe Lys Glu Ser Trp Arg Ala Leu Gln Glu
    1430                1435                1440

CGC GGC ATG TCG CAG GAC TTC AGC TGG GAG CAC GCC GCC AAG CTC TAC      2525
Arg Gly Met Ser Gln Asp Phe Ser Trp Glu His Ala Ala Lys Leu Tyr
1445                1450                1455

GAG GAC GTC CTC GTC AAG GCC AAG TAC CAG TGG  T GAACGCTAGC            2569
Glu Asp Val Leu Val Lys Ala Lys Tyr Gln Trp
1460                1465                1470

TGCTAGCCGC TCCAGCCCCG CATGCGTGCA TGACAGGATG GAACTGCATT GCGCACGCAG    2629

GAAAGTGCCA TGGAGCGCCG GCATCCGCGA AGTACAGTGA CATGAGGTGT GTGTGGTTGA    2689

GACGCTGATT CCAATCCGGC CCGTAGCAGA GTAGAGCGGA GGTATATGGG AATCTTAACT    2749

TGGTATTGTA ATTTGTTATG TTGTGTGCAT TATTACAATG TTGTTACTTA TTCTTGTTAA    2809

AAAAAAAAAA AAAAAA                                                    2825

(2) INFORMATION FOR SEQ ID NO: 6:

(i) SEQUENCE CHARACTERISTICS:
        (A) LENGTH: 799 amino acids
        (B) TYPE: amino acid
        (D) TOPOLOGY: linear (ii) MOLECULE TYPE: protein (xi) SEQUENCE DESCRIPTION: SEQ ID NO: 6:

Met Ser Ser Ala Val Ala Ser Ala Ala Ser Phe Leu Ala Leu Ala Ser
1               5                   10                  15
```

```
Ala Ser Pro Gly Arg Ser Arg Arg Ala Arg Val Ser Ala Gln Pro
            20                  25                  30

Pro His Ala Gly Ala Gly Arg Leu His Trp Pro Pro Trp Pro Gln
            35                  40                  45

Arg Thr Ala Arg Asp Gly Ala Val Ala Leu Ala Ala Gly Lys Lys
            50                  55                  60

Asp Ala Gly Ile Asp Asp Ala Ala Ser Val Arg Gln Pro Arg Ala
65                  70                  75                  80

Leu Arg Gly Gly Ala Ala Thr Lys Val Ala Glu Arg Arg Asp Pro Val
                85                  90                  95

Lys Thr Leu Asp Arg Asp Ala Ala Glu Gly Gly Pro Ser Pro Pro
            100                 105                 110

Ala Ala Arg Gln Asp Ala Ala Arg Pro Pro Ser Met Asn Gly Met Pro
            115                 120                 125

Val Asn Gly Glu Asn Lys Ser Thr Gly Gly Gly Ala Thr Lys Asp
            130                 135                 140

Ser Gly Leu Pro Thr Pro Ala Arg Ala Pro His Pro Ser Thr Gln Asn
145                 150                 155                 160

Arg Ala Pro Val Asn Gly Glu Asn Lys Ala Asn Val Ala Ser Pro Pro
                165                 170                 175

Thr Ser Ile Ala Glu Ala Ala Ala Ser Asp Ser Ala Ala Thr Ile Ser
                180                 185                 190

Ile Ser Asp Lys Ala Pro Glu Ser Val Val Pro Ala Glu Lys Thr Pro
                195                 200                 205

Pro Ser Ser Gly Ser Asn Phe Glu Ser Ser Ala Ser Ala Pro Gly Ser
210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
                245                 250                 255

Ala Val Gln Glu Asp Leu Trp Asp Phe Lys Lys Tyr Ile Gly Phe Glu
                260                 265                 270

Glu Pro Val Glu Ala Lys Asp Asp Gly Arg Ala Val Ala Asp Asp Ala
            275                 280                 285

Gly Ser Phe Glu His His Gln Asn His Asp Ser Gly Pro Leu Ala Gly
            290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Pro Arg Tyr Gly
            340                 345                 350

Asp Tyr Glu Glu Ala Tyr Asp Val Gly Val Arg Lys Tyr Tyr Lys Ala
            355                 360                 365

Ala Gly Gln Asp Met Glu Val Asn Tyr Phe His Ala Tyr Ile Asp Gly
            370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
                405                 410                 415

Phe Cys Lys Ala Ala Val Glu Val Pro Trp His Val Pro Cys Gly Gly
            420                 425                 430
```

```
Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
        450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
        530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
            580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
        755                 760                 765

Ala Leu Gln Glu Arg Gly Met Ser Gln Asp Phe Ser Trp Glu His Ala
        770                 775                 780

Ala Lys Leu Tyr Glu Asp Val Leu Val Lys Ala Lys Tyr Gln Trp
785                 790                 795
```

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide

```
        (iii) HYPOTHETICAL: YES (iv) ANTI-SENSE: NO (v) FRAGMENT TYPE: internal (xi) SEQUENCE DESCRIPTION: SEQ ID NO: 7:

Pro Trp Ser Lys Thr Gly Gly Leu Gly Asp Val Cys
1               5                   10

(2) INFORMATION FOR SEQ ID NO: 8:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO: 8:

Pro Ser Arg Phe Glu Pro Cys Gly Leu Asn Gln Leu Tyr
1               5                   10

(2) INFORMATION FOR SEQ ID NO: 9:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO: 9:

Gly Thr Gly Gly Leu Arg Asp Thr Val Glu Asn Cys
1               5                   10
```